(12) United States Patent
Enenkel

(10) Patent No.: US 8,404,486 B2
(45) Date of Patent: Mar. 26, 2013

(54) RECOMBINATION SEQUENCES

(75) Inventor: Barbara Enenkel, Warthausen (DE)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 128 days.

(21) Appl. No.: 12/744,754

(22) PCT Filed: Nov. 28, 2008

(86) PCT No.: PCT/EP2008/066430
§ 371 (c)(1),
(2), (4) Date: Nov. 4, 2010

(87) PCT Pub. No.: WO2009/068645
PCT Pub. Date: Jun. 4, 2009

(65) Prior Publication Data
US 2011/0189729 A1 Aug. 4, 2011

(30) Foreign Application Priority Data

Nov. 30, 2007 (EP) .................... 07122004
Jun. 6, 2008 (EP) .................... 08157764

(51) Int. Cl.
*C12N 15/87* (2006.01)
(52) U.S. Cl. .................... 435/462; 435/477
(58) Field of Classification Search .................. 435/462, 435/477
See application file for complete search history.

(56) References Cited

U.S. PATENT DOCUMENTS

| 7,968,341 B2 | 6/2011 | Droge et al. | |
|---|---|---|---|
| 2003/0027337 A1 | 2/2003 | Droge et al. | |
| 2007/0148773 A1* | 6/2007 | Droge et al. | 435/455 |

FOREIGN PATENT DOCUMENTS

| WO | 96/40724 A1 | 12/1996 |
| WO | 00/52027 A1 | 9/2000 |
| WO | 01/16345 A2 | 3/2001 |
| WO | 2004/048584 A1 | 6/2004 |
| WO | 2005/017170 A2 | 2/2005 |

OTHER PUBLICATIONS

Bauer, Carl E, et al; Mutational Analysis of Integrase Arm-type Binding Sites of Bacteriophage Lambda; Journal Molecular Biology (1986) vol. 192, No. 3 pp. 513-527.

Gardner, Jeffrey F., et al; Role of *Escherichia coli* IHF Protein in Lambda Site-specific Recombination; Journal of Molecular Biology (1986) vol. 191, No. 2 pp. 181-189.

International Search Report for PCT/EP2008/066430 mailed Mar. 25, 2009.

Lee, Eunhee C., et al; Genetic Analysis of *Escherichia coli* Integration Host Factor Interactions with its Bacteriophage λ, Recognition Site; Journal of Bacteriology (1991) vol. 173, No. 2 pp. 609-617.

MacWilliams, Maria, et al; Mutational Analysis of Protein Binding Sites involved in formation of the Bacteriophage λ attL Complex; Journal of Bacteriology (1997) vol. 179, No. 4 pp. 1059-1067.

Numrych, Thomas E., et al; A Genetic Analysis of Xis and FIS Interactions with Their Bing Sites in Bacteriophage Lambda; Journal of Bacteriology (1991) vol. 173, No. 19 pp. 5954-5963.

Thompson, John F., et al; Mutations in an Integration Host Factor-Binding Site: Effect on Lambda Site-Specific Recombination and regulatory implications; Journal of Bacteriology (1986) No. 168, No. 3 pp. 1343-1351.

Yu, A. et al; Control of Prophage Integration and Excision in Bacteriophage P2: Nucleotide Sequences of the *int* Gene and *att* Sites; Gene (1989) vol. 80 pp. 1-11.

* cited by examiner

*Primary Examiner* — Michele K Joike
*Assistant Examiner* — Antonio Galisteo Gonzalez
(74) *Attorney, Agent, or Firm* — Michael P. Morris; Edward S. Lazer

(57) ABSTRACT

The present invention relates to nucleotide sequences, which are variants of att recombination sequences, involved in sequence-specific recombination of DNA in eukaryotic cells, whereby sequence specific recombination is performed by a bacteriophage lambda integrase Int. Such att recombination sequences being e.g. attP.b, attP.a, attL.a, attR.a and attR.b. The present invention further relates to a method of sequence-specific recombination of DNA in eukaryotic cells, comprising the introduction of a first DNA comprising a nucleotide sequence containing at least one recombination sequence into a cell, introducing a second DNA comprising a nucleotide sequence containing at least one further recombination sequence into a cell, and performing the sequence specific recombination by a bacteriophage lambda integrase Int, whereby at least one of said first or second DNAs is an att recombination sequence being e.g. attP.b, attP.a, attL.a, attR.a or attR.b.

24 Claims, 5 Drawing Sheets

Figure 1

```
              1                                                  50
    attP   (1) TCTGTTACAGGTCACTAATACCATCTAAGTAGTTGATTCATAGTGACTGC
    attP.b (1) GCTGTTACAGGTCACTAATACCATCTACGTAGTTGATTCATATTGTCTGC 51                                                 100
    attP  (51) ATATGTTGTGTTTTACAGTATTATGTAGTCTGTTTTTTATGCAAAATCTA
    attP.b(51) ATATCTTGTGTTTTACAGTATTATCTAGTCTGTTTTTTATCCAAAATCTA 101                                                 150
    attP (101) ATTTAATATATTGATATTTATATCATTTTACGTTTCTCGTTCAGCTTTTT
    attP.b(101) ATTTATTATATTGATATTTATATCATTTTACGTTTCTCGTTCAGCTTTTT 151                                                 200
    attP (151) TATACTAAGTTGGCATTATAAAAAAGCATTGCTTATCAATTTGTTGCAAC
    attP.b(151) TATACTAAGTTGGCATTATAAAAAAGCATTGCTTATCAATTTGTTGCAAC 201                              243
    attP (201) GAACAGGTCACTATCAGTCAAAATAAAATCATTATTTGATTTC
    attP.b(201) GAACAGGTCACTATCAGTCAAAATATAATCATTATTTGATTTC
```

Figure 2

| Vektor combination | ZsGreen-positive cells |
|---|---|
| pBI-26/ZsGreen (positive control) + pCMV SS Inth218 + pIHF | 25.4 % |
| pBI-26/attP + pZsGreen/attB + pCMV SS Inth218 + pIHF | 1.7 %[#] |
| pBI-26/attP.b + pZsGreen/attB + pCMV SS Inth218 + pIHF | 1.2 %[#] |
| pBI-26/attP.b + pZsGreen/attP.b + pCMV SS Inth218 + pIHF | 1.5%[#] |
| pBI-26/ZsGreen (positive control) + pCMV SS Inth218 | 20.0 % |
| pBI-26/attP + pZsGreen/attB + pCMV SS Inth218 | 1,1 %[#] |
| pBI-26/attP.b + pZsGreen/attB + +pCMV SS Inth218 | 0,3 %[#] |
| pBI-26/attP.b + pZsGreen/attP.b + +pCMV SS Inth218 | 0,4 %[#] |

[#] after deduction of the background fluorescence of cells, which were transfected with the corresponding plasmids, however, without adding the plasmids encoding lambda-integrase and IHF.

Figure 3

```
              1                                                  50
    attP   (1) TCTGTTACAGGTCACTAATACCATCTAAGTAGTTGATTCATAGTGACTGC
    attP.a (1) GCTGTTACAGGTCACTAATACCATCTATGTAGTTGATTCATATTGTCTGC
              51                                                100
    attP  (51) ATATGTTGTGTTTTACAGTATTATGTAGTCTGTTTTTTATGCAAAATCTA
    attP.a(51) ATATCTTGTGTTTTACAGTATTATCTAGTCTGTTTTTTATCCAAAATCTA 101                                               150
    attP (101) ATTTAATATATTGATATTTATATCATTTTACGTTTCTCGTTCAGCTTTTT
    attP.a(101)ATTTATTATATTGATATTTATATCATTTTACGTTTCTCGTTCAGCTTTTT
              151                                               200
    attP (151) TATACTAAGTTGGCATTATAAAAAAGCATTGCTTATCAATTTGTTGCAAC
    attP.a(151)TATACTAAGTTGGCATTATAAAAAAGCATTGCTTATCAATTTGTTGCAAC
              201                         243
    attP (201) GAACAGGTCACTATCAGTCAAAATAAAATCATTATTTGATTTC
    attP.a(201)GAACAGGTCACTATCAGTCAAAATATAATCATTATTTGATTTC
```

Figure 4

| Vektor combination | ZsGreen-positive cells |
|---|---|
| pBI-26/attP.b + pZsGreen/attP.b + pCMV SS Inth218 | 2.0 %[#] |
| pBI-26/attP.a + pZsGreen/attP.a + pCMV SS Inth218 | 1.9 %[#] |
| pBI-26/attP. + pZsGreen/attP + pCMV SS Inth218 | 1.9 %[#] |

\# after deduction of the background fluorescence of cells, which were transfected with the corresponding plasmids, however, without adding the plasmids encoding lambda-integrase.

Figure 5

```
                    1                                                50
       attL   (1)   CTGCTTTTTTATACTAAGTTGGCATTATAAAAAAGCATTGCTTATCAATT
       attL*  (1)   CTGCTTTTTGATACTAAGTTGGCATTATAAAAAAGCATTGCTTATCAATT
       attL.a (1)   CTGCTTTTTTATACTAAGTTGGCATTATAAAAAAGCATTGCTTATCAATT 51                                               100
       attL   (51)  TGTTGCAACGAACAGGTCACTATCAGTCAAAATAAAATCATTATTTGATT
       attL*  (51)  TGTTGCAACGAACAGGTCACTATCAGTCAAAATAAAATCATTATTTGATT
       attL.a (51)  TGTTGCAACGAACAGGTCACTATCAGTCAAAATATAATCATTATTTGATT 101
       attL   (101) TC
       attL*  (101) TC
       attL.a (101) TC
```

Figure 6

```
                    1                                                50
       attR   (1)   TCTGTTACAGGTCACTAATACCATCTAAGTAGTTGATTCATAGTGACTGC
       attR*  (1)   TCTGTTACAGGTCACTAATACCATCTAAGTAGTTGATTCATAGTGACTGC
       attR.a (1)   GCTGTTACAGGTCACTAATACCATCTATGTAGTTGATTCATATTGTCTGC
       attR.b (1)   GCTGTTACAGGTCACTAATACCATCTACGTAGTTGATTCATATTGTCTGC 51                                               100
       attR   (51)  ATATGTTGTGTTTTACAGTATTATGTAGTCTGTTTTTTATGCAAAATCTA
       attR*  (51)  ATATGTTGTGTTTTACAGTATTATGTAGTCTGTTTTTTATGCAAAATCTA
       attR.a (51)  ATATCTTGTGTTTTACAGTATTATCTAGTCTGTTTTTTATCCAAAATCTA
       attR.b (51)  ATATCTTGTGTTTTACAGTATTATCTAGTCTGTTTTTTATCCAAAATCTA 101                                              150
       attR   (101) ATTTAATATATTGATATTTATATCATTTTACGTTTCTCGTTCAGCTTTTT
       attR*  (101) ATTTAATATATTGATATTTATATCATTTTACGTTTCTCGTTCAGCTTTTT
       attR.a (101) ATTTATTATATTGATATTTATATCATTTTACGTTTCTCGTTCAGCTTTTT
       attR.b (101) ATTTATTATATTGATATTTATATCATTTTACGTTTCTCGTTCAGCTTTTT 151     162
       attR   (151) TATACTAACTTG
       attR*  (151) GATACTAACTTG
       attR.a (151) TATACTAACTTG
       attR.b (151) TATACTAACTTG
```

*Figure 7*

| Substrate Vectors | ZsGreen-positive cells [%] | Recombination positive cells* [%] | X-Mean (mock cells = 13) |
|---|---|---|---|
| pBI-26/ZsGreen (= positive control, transfection efficiency) | 23.8 | - | 733 |
| pBI-26/attL + pZsGreen/attR | 3.2 | 13.4 | 216 |
| pBI-26/attL.a + pZsGreen/attR.a | 2.3 | 9.7 | 164 |
| pBI-26/attL.a + pZsGreen/attR.b | 1.2 | 5.0 | 96 |

\* Percentage of recombination positive cells in successfully transfected cells whereby calculation is based on an average transfection efficiency of 23.8% achieved with positive control cells.

*Figure 8*

| Substrate Vectors | ZsGreen-positive cells [%] | Recombination positive cells* [%] | X-Mean (mock cells = 15) |
|---|---|---|---|
| pBI-26/ZsGreen (= positive control, transfection efficiency) | 22.0 | - | 640 |
| pBI-26/attL + pZsGreen/attB | 2.3 | 10.5 | 219 |
| pBI-26/attL.a + pZsGreen/attB | 2.0 | 9.1 | 403 |
| pBI-26/attP + pZsGreen/attR | 2.3 | 10.5 | 104 |
| pBI-26/attP + pZsGreen/attR.a | 1.5 | 6.8 | 65 |
| pBI-26/attP + pZsGreen/attR.b | 1.1 | 5.0 | 73 |

\* Percentage of recombination positive cells in successfully transfected cells whereby calculation is based on an average transfection efficiency of 22 % achieved with positive control cells.

RECOMBINATION SEQUENCES

This application is the national phase entry under 35 U.S.C. §371 of International Application No. PCT/EP2008/066430, filed Nov. 28, 2008, which claims priority to European Patent Applications No. 07122004.0, filed Nov. 30, 2007 and European Patent Application 08157764.5, filed Jun. 6, 2008 which are hereby incorporated by reference in their entireties.

SEQUENCE LISTING

The instant application contains a Sequence Listing which has been submitted in ASCII format via EFS-Web and is hereby incorporated by reference in its entirety. Said ASCII copy, created on Oct. 24, 2012, is named 01-2313.txt and is 5,603 bytes in size.

BACKGROUND OF THE INVENTION

1. Technical Field

The present invention relates to novel nucleotide sequences, which are variants of att recombination sequences, involved in sequence-specific recombination of DNA in eukaryotic cells, whereby sequence specific recombination is performed by a bacteriophage lambda integrase Int. Such novel att recombination sequences being e.g. attP.b, attP.a, attL.a, attR.a and attR.b.

The present invention further relates to a method of sequence-specific recombination of DNA in eukaryotic cells, comprising the introduction of a first DNA comprising a nucleotide sequence containing at least one recombination sequence into a cell, introducing a second DNA comprising a nucleotide sequence containing at least one further recombination sequence into a cell, and performing the sequence specific recombination by a bacteriophage lambda integrase Int, whereby at least one of said first or second DNAs is a novel att recombination sequences being e.g. attP.b, attP.a, attL.a, attR.a and attR.b.

2. Background

The controlled manipulation of eukaryotic genomes and the expression of recombinant proteins from episomal vectors are important methods for analyzing the function(s) of specific genes in living organisms. Moreover, said manipulations play a role in gene therapeutic methods in medicine. In this context the generation of transgenic animals, the change of genes or gene segments (so-called "gene targeting") and the targeted integration of foreign DNA into the genome of higher eukaryotes are of particular importance. Recently these technologies could be improved by means of characterization and application of sequence specific recombination systems.

Furthermore, sequence-specific integration of expression cassettes, encoding and expressing a desired polypeptide/product, into the genome of biotechnological relevant host cells also gets more significance for the production of biopharmaceuticals. Expression level for a desired polypeptide in a stable transformed cell lines depends on the site of integration. By sequence specific integration, sites could be preferably used having a high transcription activity. The conventional method for generating production cell lines expressing a desired polypeptide/product is based on the random integration of the recombinant expression vector into the genome of the host cell. Variations in the expression level of the integrated gene(s) of interest in stable transformed cell lines are attributed mainly to differences in chromosomal locations and copy numbers. Random integration in the proximity of heterochromatin results in variable levels of transgene expression. Chromosome locations promoting the expression of the integrated gene(s) of interest are thought to be transcriptionally active regions of euchromatin. This randomness of integration causes a large diversity in recombinant cells robustness, productivity and quality, necessitating an elaborate screening process to identify and isolate a suitable cell clone expressing the desired polypeptide at high level. In addition, the heterogeneity also means that for each clone an optimized production process has to be developed, making the development of a suitable production cell line a time consuming, labor intensive and costly process.

Conservative sequence specific DNA recombinases have been divided into two families. Members of the first family, the so-called "integrase" family, catalyze the cleavage and rejoining of DNA strands between two defined nucleotide sequences, which will be named as recombination sequences in the following. The recombination sequences may be either on two different or on one DNA molecule, resulting in inter- or intramolecular recombination, respectively. For intramolecular recombination, the result of the reaction depends on the respective orientation of the recombination sequences to each other. In the case of an inverted, i.e. opposite orientation of the recombination sequences, inversion of the DNA segments lying between the recombination sequences occurs. In the case of direct, i.e. tandem repeats of the recombination sequences on a DNA substrate, a deletion occurs. In case of the intermolecular recombination, i.e. if both recombination sequences are located on two different DNA molecules, a fusion of the two DNA molecules may occur. While members of the integrase family usually catalyze both intra- as well as intermolecular recombination, the recombinases of the second family of the so-called "invertases/resolvases" are only able to catalyze the intramolecular recombination.

At present, the recombinases which are used for the manipulation of eukaryotic genomes belong to the integrase family. Said recombinases are the Cre recombinase of the bacteriophage P1 and the Flp recombinase from yeast. The recombination sequences to which the Cre recombinase binds are named loxP. LoxP is a 34 bp long nucleotide sequence consisting of two 13 bp long inverted nucleotide sequences and an 8 bp long spacer lying between the inverted sequences. The FRT named binding sequences for Flp are build up similarly. However, they differ from loxP. Therefore, the recombination sequences may not be replaced by each other, i.e. Cre is not able to recombine FRT sequences and FLP is not able to recombine loxP sequences. Both recombination systems are active over long distances, i.e. the DNA segment to be inverted or deleted and flanked by two loxP or FRT sequences may be several 10 000 base pairs long.

So far three members of the invertase/resolvase family have been used for the manipulation of eukaryotic genomes. A mutant of the bacteriophage Mu invertase Gin can catalyze the inversion of a DNA fragment in plant protoplasts without cofactors. However, it has been discovered that this mutant is hyper-recombinogenic, i.e. it catalyzes DNA strand cleavages also at other than its naturally recombination sequences. This leads to unintended partially lethal recombination events in plant protoplast genomes. The β-recombinase from *Streptococcus pyogenes* catalyses the recombination in mouse cell cultures between two recombination sequences as direct repeats leading to the excision of the segment. However, simultaneously with deletion also inversion has been detected which renders the controlled use of the system for manipulation of eukaryotic genomes unsuitable. Mutants of the 78 resolvase from *E. coli* have been shown to be active on episomal and artificially introduced genomic recombination sequences, but the efficiency of the latter reaction is still rather poor.

The manipulation of eukaryotic genomes with the Cre and Flp recombinase, respectively, shows significant disadvantages. In case of deletion, i.e. the recombination of two tandem repeated loxP or FRT recombination sequences in a genome there is an irreversibly loss of the DNA segment lying between the tandem repeats. Thus, a gene located on this DNA segment will be lost permanently for the cell and the organism. Therefore, the reconstruction of the original state for a new analyses of the gene function, e.g. in a later developmental stage of the organism, is impossible. The irreversible loss of the DNA segment caused by deletion may be avoided by an inversion of the respective DNA segment. A gene may be inactivated by an inversion without being lost and may be switched on again at a later developmental stage or in the adult animal by means of a timely regulated expression of the recombinase via back recombination. However, the use of both Cre and Flp recombinases in this modified method has the disadvantage that the inversion cannot be regulated as the recombination sequences will not be altered as a result of the recombination event. Thus, repeated recombination events occur causing the inactivation of the respective gene due to the inversion of the respective DNA segment only in some, at best in 50% of the target cells at equilibrium of the reaction. There have been efforts to solve this problem, at least in part, by constructing mutated loxP sequences which cannot be used for further reaction after a single recombination. However, the disadvantage is the uniqueness of the reaction, i.e. there is no subsequent activation by back recombination after inactivation of the gene by inversion.

A further disadvantage of the Flp recombinase is its reduced heat stability at 37° C. thus limiting the efficiency of the recombination reaction in higher eukaryotes significantly, e.g. in mice with a body temperature of about 39° C. Therefore, Flp mutants have been generated which exhibit a higher heat stability as the wild-type recombinase. However, even these mutant Flp enzymes still exhibit a lower recombination efficiency than the Cre recombinase.

A further use of sequence specific recombinases resides in the medical field, e.g. in gene therapy, where the recombinases integrate a desired DNA segment into the genome of a respective human target cell in a stable and controlled way. Both Cre and Flp may catalyze intermolecular recombination. Both recombinases recombine a plasmid DNA which carries a copy of its respective recombination sequence with a corresponding recombination sequence which has been inserted before into the eukaryotic genome via homologous recombination. However, it is desirable that this reaction includes a "naturally" occurring recombination sequence in the eukaryotic genome. Because loxP and FRT are 34 and 54 nucleotides long, respectively, occurrence of exact matches of these recombination sequences as part of the genome is statistically unlikely. Even if a recombination sequence would be present, the disadvantage of the aforementioned back reaction still exists, i.e. both Cre and Flp recombinase may excise the inserted DNA segment after successful integration by intramolecular recombination.

Thus, one problem of the present invention is to provide a simple and controllable recombination system, and the required working means. A further problem of the present invention is the provision of a recombination system and the required working means, which may carry out a stable and targeted integration of a desired DNA sequence. A further problem of the present invention is the provision of methods which allow the generation of an improved protein expression system on the basis of one of those recombination systems.

SUMMARY OF THE INVENTION

A solution is offered by using the bacteriophage lambda integrase Int recombination system and att recombination sequences. The patent applications WO01/16345 and WO2004/048584 are incorporated by reference herein.

A specific problem of the present invention is to provide alternative att sequences, which are especially modified to expand their functionality beyond mediating site-specific recombination in eukaryotic systems when operatively linked to sequences of a gene of interest.

Substitutions, deletions, and/or insertions can be introduced into attB, attP, attL and/or attR sequences or their derivatives in order to confer for example an enhancement of the recombination events driven by a wild-type or modified integrase of the bacteriophage lambda, whereby said enhancement may consist for example of (i) increasing the efficiency of recombination events (integration and/or excision), (ii) increasing the specificity of recombination, (iii) favoring excisive recombination events, (iv) favoring integrative recombination events, (v) relieving the requirements for some or all host factors, in comparison to the corresponding naturally occurring recombination sequences using the same recombinase under the same conditions. Alternatively, to not only use the att sequences as mediators for site-specific recombination but to expand their functionality by using them for example in addition as regulatory sequences substitutions, deletions, and/or insertions can also be introduced into attB, attP, attL and/or attR sequences or their derivatives to remove, change, generate or add sequences/nucleotides which may act as cis-acting sites such as (cryptic) splice donor, acceptor sites and branch points, polyadenylation signals, TATA-boxes, chi-sites, ribosomal entry sites, repeat sequences, secondary structures (e.g. stem loops), binding sites for transcription factors or other regulatory factors, restriction enzyme sites etc. to give just a few, but not limiting examples.

Substitutions were introduced into attP, attL and attR sequences. Surprisingly, some att sequences/att-variants are described in the present invention, which work especially well. Unexpectedly, some preferred att variants were still able to mediate site-specific recombinations even though substitutions are located in the binding sites for IHF, XIS, FIS and/or Int.

DESCRIPTION OF THE FIGURES

The invention is explained in more detail with the following illustrations.

FIG. 1: Alignment of the Original attP Sequence with the attP-Variant attP.b

Figure 9:
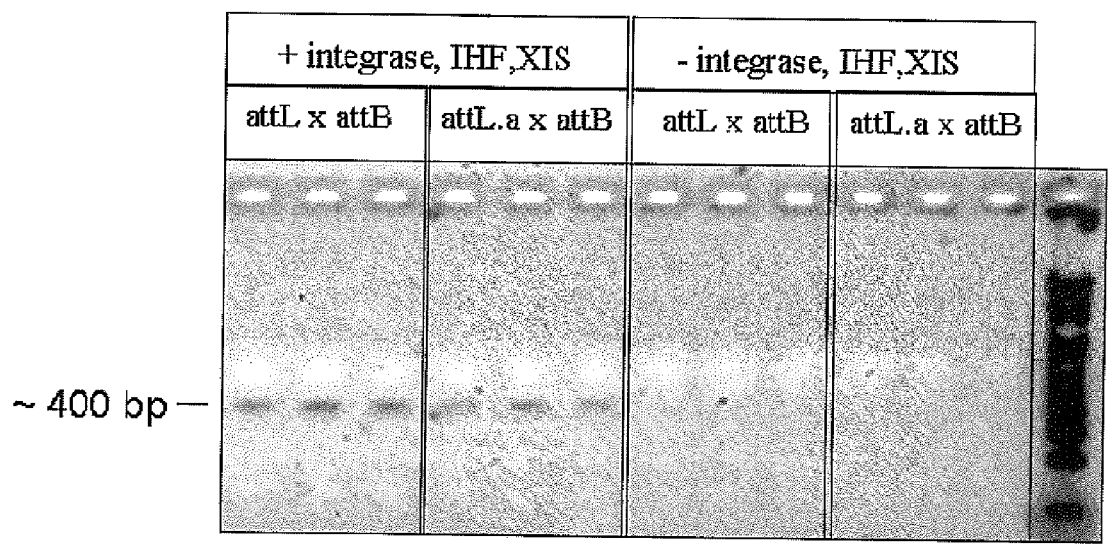

The attP variant attP.b (SEQ ID NO: 3) contains 9 substitutions, highlighted in bold letters with underlining, in comparison to the attP wildtype sequence (SEQ ID NO: 2). This is equivalent to a sequence homology of 96.3%.

FIG. 2: Intermolecular Recombination Using an attP Variant and attP Wildtype in CHO-DG44 Cells Adapted to Growth in Suspension Culture CHO-DG44 cells, which were adapted to growth in suspension culture, were transfected with lambda integrase Int-h/218 encoding plasmid at first and as the case may be with IHF encoding plasmids in serum-free medium.

24 hours post first transfection those cells were transfected in a second transfection with a combination of various substrate vectors: pBI-26/attP (attP wildtype sequence; SEQ ID NO:2)+pZsGreen/attB (attB wildtype sequence; SEQ ID NO:1), pBI-26/attP.b (attP variant; SEQ ID NO:3)+pZs-Green/attB (attB wildtype sequence; SEQ ID NO:1) and pBI-26/attP.b (attP variant; SEQ ID NO:3)+pZsGreen/attP.b (attP variant; SEQ ID NO:3).

As a positive control and for the determination of transfection efficiency the expression plasmid pBI-267ZsGreen was used. pBI-26/ZsGreen expresses a green fluorescent protein under the control of a CMV-promoter.

48 hours post second transfection the cells were analysed using FACS-analysis and the fraction of fluorescent cells was determined.

The fraction of fluorescent cells with intracellular recombination between attP.b and attB substrate vectors is on average 1.2%, between attP.b and attP.b substrate vectors on average 1.5% and between attP and attB substrate vectors on average 1.7% (mean value from 6 transfected cell pools each), when the cells were previously transfected using integrase and IHF expression vectors.

For cells, which were merely pre-transfected using the integrase expression vector, the fraction of fluorescent cells with intermolecular recombinations between attP.b and attB substrate vectors is on average 0.3%, between attP.b and attP.b substrate vectors on average 0.4% and between attP and attB substrate on average 1.1% (mean value from 6 transfected cell pools each).

In all cases described above the background fluorescence was subtracted first based on FACS analysis of cells, which were transfected using the corresponding plasmids, but without adding the plasmids encoding lambda-integrase and IHF.

FIG. 3: Alignment of the Original attP Sequence with attP Variant attP.a

The attP variant attP.a (SEQ ID NO: 4) contains 9 substitutions in comparison to the attP wildtype sequence (SEQ ID NO: 2). These substitutions, indicated by bold letters with underlining, are equivalent to a sequence homologies of 96.3%.

FIG. 4: Intermolecular Recombination Using attP Variants attP.a, attP.b and attP Wildtype in CHO-DG44 Cells Adapted to Growth in Suspension Culture Suspension adapted CHO-DG44 cells were transfected in serum-free medium with the plasmid combinations pBI-26/attP.b (attP variant; SEQ ID NO:3)+pZsGreen/attP.b (attP variant; SEQ ID NO:3), pBI-26/attP.a (attP variant; SEQ ID NO:4)+pZsGreen/attP.a (attP variant; SEQ ID NO:4) or pBI-26/attP (attP wildtype; SEQ ID NO:2)+pZsGreen/attP (attP wildtype; SEQ ID NO:2). In all cases cells were co-transfected with the plasmid pCMV SS Inth218 which encodes for lambda integrase Int-h/218.

As a negative control to determine background fluorescence mock-transfected cells were generated. 72 hours post transfection the cells were analysed using FACS-analysis and the portion of fluorescent cells was determined.

The fraction of fluorescent cells accounts on average for 2% of the cells for intermolecular recombinations between attP.b substrate vector pairs, for 1.9% of the cells for intermolecular recombinations between attP.a substrate vector pairs and for 1.9% of the cells for intermolecular recombination between attP substrate vector pairs (mean value from 3 transfected cell pools each).

In all cases described above the background fluorescence was subtracted first based on FACS analysis of cells, which were transfected using the corresponding plasmid combination, but with the addition of an empty vector as a mock plasmid rather than the lambda integrase plasmid.

FIG. 5: Alignment of the Original attL Sequence with the attL Variants attL* and attL.a Each of the attL variants attL.a (SEQ ID NO: 7) attL* (SEQ ID NO:6) contains 1 substitution in comparison to the attL wildtype sequence (SEQ ID NO: 12). These substitutions, indicated by bold letters with underlining, are equivalent to a sequence homology of 99%.

FIG. 6: Alignment of the Original attR Sequence with the attR Variants attR*, attR.a and attR.b The attR variants attR.a (SEQ ID NO:10) and attR.b (SEQ ID NO:11) contain each 8 substitutions and attR* (SEQ ID NO:8) 1 substitution in comparison to the attR wildtype sequence (SEQ ID NO:13). These substitutions, indicated by bold letters with underlining, are equivalent to a sequence homology of 95% and 99.4%, respectively.

FIG. 7: Intermolecular Recombination Between attL and attR Variants

In a first step, CHO-DG44 cells are transfected with plasmids encoding for lambda integrase Int-h/218, IHF and XIS. 24 hours post first transfection those cells are transfected in a second transfection with a combination of various attL and attR substrate vectors (n=3). As a positive control and for the determination of transfection efficiency the expression plasmid pBI-26/ZsGreen encoding a green fluorescent protein under the control of a CMV promoter is used. 48 hours post second transfection the cells are analysed using FACS-analysis and the fraction of fluorescent cells and the mean relative ZsGreen fluorescence (X-mean) is determined. In all cases the background fluorescence is subtracted first based on FACS analysis of cells, which are transfected with the identical substrate vector combination corresponding plasmids in the second transfection but are only mock-transfected in the first transfection.

FIG. 8: Intermolecular Cross-Recombination Between attL and attB Variants and attP and attR Variants In a first step, CHO-DG44 cells are transfected with plasmids encoding for lambda integrase Int-h/218, IHF and XIS. 24 hours post first transfection those cells are transfected in a second transfection with a combination of various attL and attB or attP and attR substrate vectors (n=3). As a positive control and for the determination of transfection efficiency the expression plasmid pBI-26/ZsGreen encoding a green fluorescent protein under the control of a CMV promoter is used. 48 hours post second transfection the cells are analysed using FACS-analysis and the fraction of fluorescent cells and the mean relative ZsGreen fluorescence is determined. In all cases the background fluorescence is subtracted first based on FACS analysis of cells, which are transfected with the identical substrate vector combination corresponding plasmids in the second transfection but are only mock-transfected in the first transfection.

FIG. 9: Verification of Cross-Recombination by PCR

PCR on plasmid DNA isolated from cell pools transfected with either the attL and attB or attL.a and attB substrate vector combination, is performed using the primer combination CENfor2 and ZsGrev1. In case of a successful intermolecular recombination between the pair of substrate vectors ZsGreen positioned on the pZsGreen/att-vectors comes under the control of the CMV enhancer/promoter located on the pBI-26/att-vectors with the corresponding attachment site between them. As a consequence, a PCR product with the above mentioned primers should only occur in case of successful recombination events. And indeed, in all cell pools pre-transfected with pCM SS Inth218, pIHF and pBI/TI-X followed by a second transfection with pairs of substrate vectors the expected PCR product of 400 bp is detected. No PCR product is obtained in mock pre-transfected cell pools transfected in a second transfection with pairs of substrate vectors.

DETAILED DESCRIPTION OF THE INVENTION

The general embodiments "comprising" or "comprised" encompass the more specific embodiment "consisting of". Furthermore, singular and plural forms are not used in a limiting way.

Terms used in the course of this present invention have the following meaning

The term "transformation" or "to transform", "transfection" or "to transfect" as used herein means any introduction of a nucleic acid sequence into a cell, resulting in genetically modified, recombinant, transformed or transgenic cells. The introduction can be performed by any method well known in the art. Methods include but are not limited to lipofection, electroporation, polycation (such as DEAE-dextran)-mediated transfection, protoplast fusion, viral infections and microinjection or may be carried out by means of the calcium method, electroshock method, intravenous/intramusuclar injection, aerosol inhalation or an oocyte injection. The transformation may result in a transient or stable transformation of the host cells. The term "transformation" or "to transform" also means the introduction of a viral nucleic acid sequence in a way which is for the respective virus the naturally one. The viral nucleic acid sequence needs not to be present as a naked nucleic acid sequence but may be packaged in a viral protein envelope. Thus, the term relates not only to the method which is usually known under the term "transformation" or "to transform". Transfection methods that provide optimal transfection frequency and expression of the introduced nucleic acid are favored. Suitable methods can be determined by routine procedures. For stable transfectants the constructs are either integrated into the host cell's genome or an artificial chromosome/mini-chromosome or located episomally so as to be stably maintained within the host cell.

The term "recombination sequences" as used herein relates to att sequences, any derivatives or homologues thereof, preferably to attB (SEQ ID NO:1), attP (SEQ ID NO:2), attL (SEQ ID NO:12) and attR (SEQ ID NO: 13) sequences and the derivatives thereof such as the exemplary sequences attP.b specified in SEQ ID NO:3, attP.a specified in SEQ ID NO:4, attL* specified in SEQ ID NO:6, attL.a specified in SEQ ID NO:7, attR* specified in SEQ ID NO:8, attR.a as specified in SEQ ID NO:10 and attR.b specified in SEQ ID NO:11.

The term "derivative" or "variant" as used herein relates to attB, attP, attL and attR sequences as well as attP.b, attP.a, attL*, attL.a, attR*, attR.a and attR.b having one or more substitutions, preferably seven, more preferably two, three, four, five or six in the overlap region and/or core region in contrast to naturally occurring attB, attP, attL and attR sequences. The term "derivative" or "variant" also relates to at least one core Int binding site of attB, attP, attL or attR. The term "derivative" or "variant" also relates to at least one core Int binding site of attP, attL or attR plus one or more copies of the arm-binding sites for Int. The term "derivative" or "variant" also relates to at least one core Int binding site of attP, attL or attR plus one or more copies of the IHF, FIS or XIS factor binding sites. The term "derivative" also relates to a combination of these features. The term "derivative" also relates to substitutions in the IHF, FIS or XIS factor binding site or in the Int arm binding sites. The term "derivative" or "variant" moreover relates to any functional fragments thereof and to endogenous nucleotide sequences in eukaryotic cells supporting sequence-specific recombination, e.g. attH identified in the human genome (see e.g. WO 01/16345).

The term "derivative" or "variant" in general includes attB, attP, attL or attR sequences suitable for realizing the intended use of the present invention, which means that the sequences mediate sequence-specific recombination events driven by an integrase (wild-type or modified) of the bacteriophage lambda.

The term "functional fragment" relates to attB, attP, attL, attR, attP.b, attP.a, attL*, attL.a, attR*, attR.a and attR.b sequences having substitutions, deletions, and/or insertions (including presence or absence of wild-type or modified protein binding sites), which can mediate sequence-specific recombination driven by an wild-type or modified integrase of the bacteriophage lambda in spite of the modifications. Substitutions, deletions, and/or insertions can be introduced into attB, attP, attL and/or attR sequences or their derivatives in order to confer for example an enhancement of the recombination events driven by a wild-type or modified integrase of the bacteriophage lambda, whereby said enhancement may consist for example of (i) increasing the efficiency of recombination events (integration and/or excision), (ii) increasing the specificity of recombination, (iii) favoring exclusive recombination events, (iv) favoring integrative recombination events, (v) relieving the requirements for some or all host factors, in comparison to the corresponding naturally occurring recombination sequences using the same recombinase under the same conditions. Substitutions, deletions, and/or insertions can also be introduced into attB, attP, attL and/or attR sequences or their derivatives to remove, change, generate or add for example nucleotide tripletts which might act as start codon (ATG) or stop codon (TAA, TAG, TGA) in a recombination sequence or encode for certain amino acids when operatively linked (fused) in reading frame to a gene sequence coding for a gene of interest. Alternatively, to not only use the att sequences as mediators for site-specific recombination but to expand their functionality by using them for example in addition as regulatory sequences substitutions, deletions, and/or insertions can also be introduced into attB, attP, attL and/or attR sequences or their derivatives to remove, change, generate or add sequences/nucleotides which may act as cis-acting sites such as (cryptic) splice donor, acceptor sites and branch points, polyadenylation signals, TATA-boxes, chi-sites, ribosomal entry sites, repeat sequences, secondary structures (e.g. stem loops), binding sites for transcription factors or other regulatory factors, restriction enzyme sites etc. to give just a few, but not limiting examples.

The functionality of modified recombination sites or of modified integrase can be demonstrated in ways that depend on the desired particular characteristic and are known in the art. For example, a co-transfection assay as described in the present invention (see Example 1) may be used to characterize integrase-mediated recombination of extrachromosomal DNA in a variety of cell lines. Briefly, cells are co-transfected with an expression vector encoding the integrase protein, optionally also vectors encoding for co-factors such as IHF, XIS and/or FIS might be added, and a substrate vector that is a substrate for the recombinase, encoding a functional/non-functional reporter gene (e.g. fluorescent protein like GFP) and containing at least one recombination sequence therein. Upon expression of the integrase by the expression vector, the function of the reporter gene will be rendered non-functional/functional. Thus, the recombination activity can be assayed either by recovering the recombined substrate vector and looking for evidence of recombination at the DNA level (for example by performing a PCR, sequence analysis of the recombined region, restriction enzyme analysis, Southern blot analysis) or by looking for evidence of the recombination at the protein level (e.g. ELISA, Western Blotting, radioimmunoassay, immunoprecipitation, immunostaining, FACS-analysis of fluorescent proteins).

The term "overlap region" as used herein defines the sequence of the recombination sequences where the DNA strand exchange, including strand cleavage and religation, takes place and relates to the consensus DNA sequence 5'-TTTATAC-3' in wild-type att sites or said sequence having functional nucleotide substitutions. The only prerequisite is, that the sequence of the overlap region is identical between recombining partner sequences.

The term "core binding sites" relates to two imperfectly repeated copies in inverted orientation, separated by the overlap region, in each set of wild-type att sites. The core binding sites are essential for the recombination by binding the integrase at low affinity. Each core binding site consists of nine contiguous base pairs and relates to DNA sequences consisting for the B-sequence of the nucleotide sequence 5'-CTGCTTTTT-3', for the B'-sequence of the nucleotide sequence 5'-CAAGTTAGT-3' (reverse complementary strand), for the C-sequence of the nucleotide sequence 5'-CAGCTTTTT-3', and for the C'-sequence of the nucleotide sequence 5'-CAACTTAGT-3' (reverse complementary strand) in wild-type att sites or said sequences having functional nucleotide substitutions.

The term "arm-binding site for Int" or "arm-binding sites" as used herein relates to the consensus sequence 5'-C/AAGTCACTAT-3' (embodiments disclosed as SEQ ID NOS 5 and 9) or said sequence having functional nucleotide substitutions. The arm-binding site for Int may be positioned at various distances upstream and/or downstream of the core Int binding site(s).

The term "homologue" or "homologous" or "similar" as used herein with regard to recombination sequences, overlap regions, core binding sites, arm-binding sites, and host factor binding sites relates to a nucleic acid sequence being identical to at least 70%, preferably to at least 75%, more preferably to at least 80%, even more preferably to at least 85%, further more preferably to at least 90%, further more preferably to at least 95%, and most preferably to at least 99% to naturally occurring recombination sequences, overlap regions, core binding sites, arm-binding sites, and host factor binding sites. As homologous or similar are considered sequences, which e.g. using standard parameters in the similarity algorithm BLAST of NCBI showing a probability of $P<10^{-5}$ when compared to the recombination sequences.

The term "vector" as used herein relates to naturally occurring or synthetically generated constructs for uptake, proliferation, expression or transmission of nucleic acids in a cell, e.g. plasmids, phagemids, cosmids, artificial chromosomes/mini-chromosomes, bacteriophages, viruses or retro viruses. Methods used to construct vectors are well known to a person skilled in the art and described in various publications. In particular techniques for constructing suitable vectors, including a description of the functional and regulatory components such as promoters, enhancers, termination and polyadenylation signals, selection markers, origins of replication, and splicing signals, are known to the person skilled in the art. The eukaryotic expression vectors will typically contain also prokaryotic sequences that facilitate the propagation of the vector in bacteria such as an origin of replication and antibiotic resistance genes for selection in bacteria. A variety of eukaryotic expression vectors, containing a cloning site into which a polynucleotide can be operatively linked, are well known in the art and some are commercially available from companies such as Stratagene, La Jolla, Calif.; Invitrogen, Carlsbad, Calif.; Promega, Madison, Wis. or BD Biosciences Clontech, Palo Alto, Calif.

The terms "gene of interest", "desired sequence", or "desired gene" as used herein have the same meaning and refer to a polynucleotide sequence of any length that encodes a product of interest. The selected sequence can be full length or a truncated gene, a fusion or tagged gene, and can be a cDNA, a genomic DNA, or a DNA fragment, preferably, a cDNA. It can be the native sequence, i.e. naturally occurring form(s), or can be mutated or otherwise modified as desired. These modifications include codon optimizations to optimize codon usage in the selected host cell, humanization or tagging. Furthermore they can include removal or additions of cis-acting sites such as (cryptic) splice donor, acceptor sites and branch points, polyadenylation signals, TATA-boxes, chi-sites, ribosomal entry sites, repeat sequences, secondary structures (e.g. stem loops), binding sites for transcription factors or other regulatory factors, restriction enzyme sites etc. to give just a few, but not limiting examples. The selected sequence can encode a secreted, cytoplasmic, nuclear, membrane bound or cell surface polypeptide. The "product of interest" includes proteins, polypeptides, fragments thereof, peptides, antisense RNA all of which can be expressed in the selected host cell.

The term "nucleic acid sequence", "nucleotide sequence", or "DNA sequence" as used herein refers to an oligonucleotide, nucleotide or polynucleotide and fragments and portions thereof and to DNA or RNA of genomic or synthetic origin, which may be single or double stranded and represent the sense or antisense strand. The sequence may be a non-coding sequence, a coding sequence or a mixture of both. The polynucleotides of the invention include nucleic acid regions wherein one or more codons have been replaced by their synonyms.

The nucleic acid sequences of the present invention can be prepared using standard techniques well known to one of skill in the art. The term "encoding" or "coding" refers to the inherent property of specific sequences of nucleotides in a nucleic acid, such as a gene in chromosome or an mRNA, to serve as templates for synthesis of other polymers and macromolecules in biological processes having a defined sequence of nucleotides (i.e. rRNA, tRNA, other RNA molecules) or amino acids and the biological properties resulting therefrom. Thus a gene encodes a protein, if transcription and translation of mRNA produced by that gene produces the protein in a cell or other biological system. Both the coding strand, the nucleotide sequence of which is identical to the mRNA sequence and is usually provided in sequence listings, and non-coding strand, used as the template for the transcription, of a gene or cDNA can be referred to as encoding the protein or other product of that gene or cDNA. A nucleic acid that encodes a protein includes any nucleic acids that have different nucleotide sequences but encode the same amino acid sequence of the protein due to the degeneracy of the genetic code. Nucleic acids and nucleotide sequences that encode proteins may include introns.

The term "polypeptide" is used interchangeably with amino acid residue sequences or protein and refers to polymers of amino acids of any length. These terms also include proteins that are post-translationally modified through reactions that include, but are not limited to, glycosylation, acetylation, phosphorylation or protein processing. Modifications and changes, for example fusions to other proteins, amino acid sequence substitutions, deletions or insertions, can be made in the structure of a polypeptide while the molecule maintains its biological functional activity. For example certain amino acid sequence substitutions can be made in a polypeptide or its underlying nucleic acid coding sequence and a protein can be obtained with like properties. Amino acid modifications can be prepared for example by performing site-specific mutagenesis or polymerase chain reaction mediated mutagenesis on its underlying nucleic acid sequence.

The term "expression" as used herein refers to transcription and/or translation of a heterologous nucleic acid sequence within a host cell. The level of expression of a desired product in a host cell may be determined on the basis of either the amount of corresponding mRNA that is present in the cell, or the amount of the desired polypeptide encoded by the selected sequence. For example, mRNA transcribed from a selected sequence can be quantitated by Northern blot hybridization, ribonuclease RNA protection, in situ hybridization to cellular RNA or by PCR. Proteins encoded by a selected sequence can be quantitated by various methods, e.g. by ELISA, by Western blotting, by radioimmunoassays, by immunoprecipitation, by assaying for the biological activity of the protein, or by immunostaining of the protein followed by FACS analysis PCR.

An "expression cassette" defines a region within a construct that contains one or more genes to be transcribed, wherein the genes contained within the segment are operatively linked to each other and transcribed from a single promoter, and as result, the different genes are at least transcriptionally linked. More than one protein or product can be transcribed and expressed from each transcription unit. Each transcription unit will comprise the regulatory elements necessary for the transcription and translation of any of the selected sequence that are contained within the unit.

The term "operatively linked" means that two or more nucleic acid sequences or sequence elements are positioned in a way that permits them to function in their intended manner. For example, a promoter and/or enhancer is operatively linked to a coding sequence if it acts in cis to control or modulate the transcription of the linked sequence. Generally, but not necessarily, the DNA sequences that are operatively linked are contiguous and, where necessary to join two protein coding regions or in the case of a secretory leader, contiguous and in reading frame.

The term "selection marker gene" refers to a gene that only allows cells carrying the gene to be specifically selected for or against in the presence of a corresponding selection agent. By way of illustration, an antibiotic resistance gene can be used as a positive selectable marker gene that allows the host cell transformed with the gene to be positively selected for in the presence of the corresponding antibiotic; a non-transformed host cell would not be capable of growth or survival under the selection culture conditions. Selectable markers can be positive, negative or bifunctional. Positive selectable markers allow selection for cells carrying the marker by conferring resistance to a drug or compensate for a metabolic or catabolic defect in the host cell. In contrast, negative selection markers allow cells carrying the marker to be selectively eliminated. For example, using the HSV-tk gene as a marker will make the cells sensitive to agents such as acyclovir and gancyclovir. The selectable marker genes used herein, including the amplifiable selectable genes, will include recombinantly engineered mutants and variants, fragments, functional equivalents, derivatives, homologs and fusions of the native selectable marker gene so long as the encoded product retains the selectable property. Useful derivatives generally have substantial sequence similarity (at the amino acid level) in regions or domains of the selectable marker associated with the selectable property. A variety of marker genes have been described, including bifunctional (i.e. positive/negative) markers (see e.g. WO 92/08796 and WO 94/28143), incorporated by reference herein. For example, selectable genes commonly used with eukaryotic cells include the genes for aminoglycoside phosphotransferase (APH), hygromycin phosphotransferase (HYG), dihydrofolate reductase (DHFR), thymidine kinase (TK), glutamine synthetase, asparagine synthetase, and genes encoding resistance to neomycin (G418), puromycin, histidinol D, bleomycin and phleomycin.

Selection may also be made by fluorescence activated cell sorting (FACS) using for example a cell surface marker, bacterial-galactosidase or fluorescent proteins (e.g. green fluorescent proteins (GFP) and their variants from *Aequorea victoria* and *Renilla reniformis* or other species; red fluorescent proteins, fluorescent proteins and their variants from non-bioluminescent species (e.g. *Discosoma* sp., *Anemonia* sp., *Clavularia* sp., *Zoanthus* sp.) to select for recombinant cells.

The term "selection agent" refers to a substance that interferes with the growth or survival of a host cell that is deficient in a particular selectable gene. For example, to select for the presence of an antibiotic resistance gene like APH (aminoglycoside phosphotransferase) in a transfected cell the antibiotic Geneticin (G418) is used.

The integrase (usually and designated herein as "Int") of the bacteriophage lambda belongs like Cre and Flp to the integrase family of the sequence specific conservative DNA recombinases. In its natural function Int catalyses the integrative recombination between two different recombination sequences namely attB and attP. AttB comprises 21 nucleotides and was originally isolated from the *E. coli* genome; Mizuuchi, M. and Mizuuchi, K. (1980) Proc. Natl. Acad. Sci. USA, 77, pp. 3220. On the other hand attP having 243 nucleotides is much longer and occurs naturally in the genome of the bacteriophage lambda; Landy, A. and Ross, W. (1977) Science, 197, pp. 1147. The Int recombinase has seven binding sites altogether in attP and two in attB. The biological function of Int is the sequence specific integration of the circular phage genome into the locus attB on the *E. coli* chromosome. Int needs a protein co-factor, the so-called integration host factor (usually and designated herein as "IHF") for the integrative recombination; Kikuchi, Y. and Nash, H. (1978) J. Biol. Chem., 253, 7149. IHF is needed for the assembly of a functional recombination complex with attP. A second co-factor for the integration reaction is the DNA negative supercoiling of attP. Finally, the recombination between attB and attP leads to the formation of two new recombination sequences, namely attL and attR, which serve as substrate and recognition sequence for a further recombination reaction, the excision reaction. A comprehensive summary of the bacteriophage lambda integration is given e.g. in Landy, A. (1989) Annu Rev. Biochem., 58, pp. 913.

The excision of the phage genome out of the bacterial genome is catalyzed by the Int recombinase also. For this, a further co-factor is needed in addition to Int and IHF, which is encoded by the bacteriophage lambda. This is the excisionase (usually and designated herein as "XIS") having two binding sites in attR; Gottesman, M. and Weisberg, R. (1971) The Bacteriophage Lambda, Cold Spring Harbor Laboratory, pp. 113. In contrast to the integrative recombination, DNA negative supercoiling of the recombination sequences is not necessary for the exclusive recombination. However, DNA negative supercoiling increases the efficiency of the recombination reaction. A further improvement of the efficiency of the excision reaction may be achieved with a second co-factor namely FIS (factor for inversion stimulation), which acts in conjunction with XIS; Landy, A. (1989) Annu Rev. Biochem., 58, pp. 913. The excision is genetically the exact reverse reaction of the integration, i.e. attB and attP are generated again. A comprehensive summary of the bacteriophage lambda excision is given e.g. in Landy, A. (1989) Annu Rev. Biochem., 58, pp. 913.

The present invention relates to a nucleic acid molecule selected from the group consisting of attP.b (SEQ ID NO:3), attP.a (SEQ ID NO:4), attL* (SEQ ID NO:6), attL.a (SEQ ID NO:7), attR* (SEQ ID NO:8), attR.a (SEQ ID NO:10) and attR.b (SEQ ID NO:11) or a derivative or homo logue thereof.

The present invention specifically relates to a nucleic acid molecule selected from the group consisting of attP.b (SEQ ID NO:3), attP.a (SEQ ID NO:4), attL* (SEQ ID NO:6), attL.a (SEQ ID NO:7), attR* (SEQ ID NO:8), attR.a (SEQ ID NO:10) and attR.b (SEQ ID NO:11).

The present invention furthermore relates to a nucleic acid molecule comprising attP.b (SEQ ID NO:3), attP.a (SEQ ID NO:4), attL* (SEQ ID NO:6), attL.a (SEQ ID NO:7), attR* (SEQ ID NO:8), attR.a (SEQ ID NO:10) or attR.b (SEQ ID NO:11) or a derivative or homologue thereof.

The present invention specifically relates to a nucleic acid molecule comprising attP.b (SEQ ID NO:3), attP.a (SEQ ID NO:4), attL* (SEQ ID NO:6), attL.a (SEQ ID NO:7), attR* (SEQ ID NO:8), attR.a (SEQ ID NO:10) or attR.b (SEQ ID NO:11).

In a further embodiment the present invention relates to a nucleic acid molecule, whereby said nucleic acid sequence mediates sequence-specific recombination of DNA in eukaryotic cells and whereby sequence specific recombination is performed by a bacteriophage lambda integrase Int. In a preferred embodiment said integrase Int is modified Int, preferably the Int-h or Int-h/218. In a further preferred embodiment said integrase Int has SEQ ID NO: 15.

The present invention furthermore relates to a vector comprising any one of the described nucleic acid molecules. In a specific embodiment said vector is a eukaryotic expression vector. In a further specific embodiment said vector comprises a promoter and/or a heterologous gene of interest and/or a selection marker and/or an enhancer. In another embodiment the selection marker is DHFR, Glutamin Synthetase or Neomycin Phosphotransferase.

The present invention further relates to a cell comprising any one of the nucleic acid molecules described in the present invention, whereby said nucleic acid molecule is integrated into the genome or in an artificial chromosome or in a minichromosome or in an episomal element or in any of the vectors of the invention. In a specific embodiment said cell is a eukaryotic cell such as a yeast, plant, worm, insect, avian, fish, reptile or mammalian cell. In a further specific embodiment said eukaryotic cell is a mammalian cell selected from the group consisting of a Chinese Hamster Ovary (CHO) cell, monkey kidney CV1 cell, monkey kidney COS cell, human lens epithelium PER.C6™ cell, human embryonic kidney HEK293 cell, human amniocyte cell, human myeloma cell, baby hamster kidney cell, African green monkey kidney cell, human cervical carcinoma cell, canine kidney cell, buffalo rat liver cell, human lung cell, human liver cell, mouse mammary tumor or myeloma cell such as NS0, a dog, pig, macaque, rat, rabbit, cat and goat cell. In a preferred embodiment said CHO cell is CHO wild type, CHO K1, CHO DG44, CHO DUKX-B11, CHO Pro-5, preferably CHO DG44.

The present invention further relates to a method of sequence specific recombination of DNA in a eukaryotic cell, comprising
a) introducing a DNA comprising a first attB, attP, attP.b, attP.a, attL, attL*, attL.a, attR, attR*, attR.a or attR.b sequence into a cell;
b) introducing a DNA comprising a second attP.b, attP.a, attL*, attL.a, attR*, attR.a or attR.b sequence into a cell, or vice versa, and
c) performing the sequence specific recombination by a bacteriophage lambda integrase Int.

In a specific embodiment of said method said first DNA sequence comprises attB sequence said second sequence comprises attP.b, attP.a, attL*, attL.a, attR*, attR.a or attR.b or vice versa.

In a further specific embodiment of said method said first DNA sequence comprises an attP.b sequence said second sequence comprises an attP.b, attP.a, attL*, attL.a, attR*, attR.a or attR.b sequence.

In a preferred embodiment of said method said first DNA sequence comprises an attP.b sequence and said second sequence comprises an attP.b sequence as well.

In a specific embodiment said method of sequence specific recombination of DNA is performed in a eukaryotic cell having integrated the first att sequence according to the invention in an artificial-/minichromosome or the genome of said eukaryotic cell. In a further preferred embodiment said method additionally comprises the steps b) and c) according to method of the invention.

In a further embodiment said method is characterized in that the first att sequence naturally occurs in the genome of said eukaryotic cell or is introduced previously.

A further aspect of the present invention is a method of expressing at least one gene of interest encoding one or more desired polypeptide(s)/product(s) in a eukaryotic cell, comprising
a) introducing a first DNA comprising an attB, attP, attP.b, attP.a, attL, attL*, attL.a, attR, attR*, attR.a or attR.b sequence into a cell;
b) introducing a second DNA comprising an attP.b, attP.a, attL*, attL.a, attR*, attR.a or attR.b sequence
or vice versa and
c) introducing at least one gene of interest into a cell;
d) contacting said cell with a bacteriophage lambda integrase Int;
e) performing the sequence-specific recombination by a bacteriophage lambda integrase Int, wherein the second DNA is integrated into the first DNA; and
f) cultivating said cell under conditions, wherein the gene(s) of interest is/are being expressed.

In a preferred embodiment said method is characterized in that the first DNA has been integrated into the host cell genome, an artificial-/minichromosome or an episomal element of the host cell, before said second DNA is introduced into said cell.

The invention further relates to a method of expressing at least one gene of interest encoding one or more desired polypeptide(s)/product(s) in a eukaryotic cell, having at least one naturally occurring recombination sequence which allows sequence-specific recombination mediated by an bacteriophage lambda Int or any functional mutant thereof, comprising introducing a DNA comprising an attP.b, attP.a, attL*, attL.a, attR*, attR.a or attR.b sequence and at least one gene of interest into said cell;
contacting said cell with a bacteriophage lambda integrase Int;
performing the sequence-specific recombination by a bacteriophage lambda integrase Int, between the recombination sequence naturally occurring in said cell and the DNA introduced into said cell; and
cultivating said cell under conditions, wherein the gene(s) of interest is/are being expressed.

The invention furthermore relates to a method of producing at least one polypeptide of interest in a eukaryotic cell, having at least one naturally occurring recombination sequence which allows sequence-specific recombination mediated by an bacteriophage lambda Int or any functional mutant thereof, comprising introducing a DNA comprising an attP.b, attP.a, attL*, attL.a, attR*, attR.a or attR.b sequence and at least one gene of interest into said cell;

contacting said cell with a bacteriophage lambda integrase Int;

performing the sequence-specific recombination by a bacteriophage lambda integrase Int, between the recombination sequence naturally occurring in said cell and the DNA introduced into said cell; and cultivating said cell under conditions, wherein the gene(s) of interest is/are being expressed.

In a preferred embodiment said method is characterized in that the naturally occurring sequence is attH. In a further preferred embodiment said method is characterized in that the naturally occurring sequence is SEQ ID NO: 14.

The invention furthermore relates to a method of producing at least one polypeptide of interest in a eukaryotic cell, having at least one recombination sequence which allows sequence-specific recombination mediated by an bacteriophage lambda Int or any functional mutant thereof, comprising introducing a DNA comprising an attP.b, attP.a, attL*, attL.a, attR*, attR.a or attR.b sequence and at least one gene of interest into said cell; contacting said cell with a bacteriophage lambda integrase Int;

performing the sequence-specific recombination by a bacteriophage lambda integrase Int, between the recombination sequence naturally occurring in said cell and the DNA introduced into said cell; and cultivating said cell under conditions, wherein the gene(s) of interest is/are being expressed.

In a preferred embodiment the methods of the invention are characterized in that said desired polypeptide(s)/product(s) is/are isolated from the host cell or the cell culture medium.

In a specific embodiment the methods of the invention are characterized in that said attP.b, attP.a, attL*, attL.a, attR*, attR.a or attR.b sequences comprise one copy or more copies of the arm-binding site(s) for Int, or wherein said sequences comprise one copy or more copies of the core Int binding site(s), or wherein said sequences comprise of a combination of one copy or more copies of the arm-binding site(s) for Int and one copy or more copies of the core Int binding site(s).

In another embodiment the methods of the invention are characterized in that said attP.b, attP.a, attL*, attL.a, attR*, attR.a or attR.b sequences consist of one copy or more copies of the core Int binding site(s).

In a preferred embodiment the methods of the invention are characterized in that said attP.b, attP.a, attL*, attL.a, attR*, attR.a or attR.b sequences consist of one copy or more copies of the core Int binding site(s) or wherein derivatives of said att-sequences consist of a combination of one copy or more copies of the arm-binding site(s) for Int and one copy or more copies of the core Int binding site(s).

In a specific embodiment the methods of the invention are characterized in that the core binding site consists of nine contiguous base pairs and relates to DNA sequences consisting of the B-sequence of the nucleotide sequence 5'-CTGCTTTTT-3', of the B'-sequence of the nucleotide sequence 5'-CAAGTTAGT-3' (reverse complementary strand), of the C-sequence of the nucleotide sequence 5'-CAGCTTTTT-3', and of the C'-sequence of the nucleotide sequence 5'-CAACTTAGT-3' (reverse complementary strand) in wild-type att sites or said sequences having functional nucleotide substitutions.

In a preferred embodiment the methods of the invention are characterized in that said sequence-specific recombination is performed by Int and one or more cofactors selected from XIS, FIS and/or IHF.

In a further preferred embodiment the methods of the invention are characterized in that the sequence-specific recombination is performed by a modified Int, preferably the Int-h or Int-h/218.

In another embodiment the methods of the invention are characterized in that Int, Int-h or Int-h/218, XIS, FIS and/or IHF are added to the cell in purified form, as mRNAs encoding for the integrase or the host factors or are co-expressed by said host cell, wherein the sequence-specific recombination is performed.

In a further embodiment the methods of the invention are characterized in that additionally a third or a third and fourth DNA sequence comprising an Int gene, or an Int gene and one or more cofactor genes selected from XIS gene, FIS gene and/or IHF gene, respectively, is/are introduced into the cell.

In a preferred embodiment the methods of the invention are characterized in that neither XIS, FIS nor IHF is required, when sequence specific recombination is performed by a modified Int, preferably the Int-h or Int-h/218.

In another preferred embodiment the methods of the invention are characterized in that said polypeptide of interest is an antibody, hormone or growth factor.

In a specific embodiment the methods of the invention are characterized in that the host cell is a mammalian cell. In a preferred embodiment the methods of the invention are characterized in that the mammalian cell is a rodent cell, preferably a mouse or a hamster cell. In a specifically preferred embodiment the methods of the invention are characterized in that the hamster cell is a BHK or CHO cell and the mouse cell is a murine myeloma cells, preferably NS0 and Sp2/0 cell.

Another aspect of the present invention relates to a method of sequence specific recombination of DNA in a eukaryotic cell, comprising a) introducing a first attB, attP, attP.b, attP.a, attL, attL*, attL.a, attR, attR*, attR.a or attR.b sequence or a derivative or homologue thereof into a cell, b) introducing a second attP.b, attP.a, attL*, attL.a, attR*, attR.a or attR.b sequence or a derivative or homologue thereof into a cell, wherein if said first DNA sequence comprises an attB sequence or a derivative or homologue thereof said second sequence comprises an attP.b, attP.a, attL*, attL.a, attR*, attR.a or attR.b sequence or a derivative or homologue thereof, or wherein if said first DNA sequence comprises an attP.b sequence or a derivative or homologue thereof said second sequence comprises an attP.b, attP.a, attL*, attL.a, attR*, attR.a or attR.b sequence or a derivative or homologue thereof or wherein if said first DNA sequence comprises an attL sequence or a derivative or homologue thereof said second sequence comprises attP.b, attP.a, attL*, attL.a, attR*, attR.a or attR.b sequence or a derivative or homologue thereof, or wherein if said first DNA sequence comprises an attR sequence or a derivative or homologue thereof said second sequence comprises an attP.b, attP.a, attL*, attL.a, attR*, attR.a or attR.b sequence or a derivative or homologue thereof, c) performing the sequence-specific recombination by a bacteriophage lambda integrase Int.

Preferred is the method wherein in step c) the sequence-specific recombination is performed by Int or by Int and XIS, FIS, and/or IHF. Most preferred is the method wherein in step c) the sequence-specific recombination is performed by Int or by Int and a XIS factor, or by Int and IHF, or by Int and XIS and IHF. Further preferred is the method wherein in step c) the sequence-specific recombination is performed by a modified Int, preferably the Int-h or Int-h/218. In this context, use of a modified Int together with XIS, FIS and/or IHF is also within the meaning of the present invention.

In a more preferred embodiment of this method, sequence specific recombination of DNA in a eukaryotic cells will be performed between identically or nearly identically recombination sites. Therefore, the present invention relates a method of sequence specific recombination as described above, wherein if said first DNA sequence comprises an attP.b sequence or a derivative or homologue thereof said second sequence comprises also attP.b sequence or a derivative or homologue thereof, or wherein if said first DNA sequence comprises an attP.a sequence or a derivative or homologue thereof said second sequence comprises an attP.a sequence or a derivative or homologue thereof, or wherein if said first DNA sequence comprises an attL* sequence or a derivative or homologue thereof said second sequence comprises an attL* sequence or a derivative or homologue thereof, or wherein if said first DNA sequence comprises an attL.a sequence or a derivative or homologue thereof said second sequence comprises an attL.a sequence or a derivative or homologue thereof, or wherein if said first DNA sequence comprises an attR* sequence or a derivative or homologue thereof said second sequence comprises an attR* sequence or a derivative or homologue thereof, or wherein if said first DNA sequence comprises an attR.a sequence or a derivative or homologue thereof said second sequence comprises an attR.a sequence or a derivative or homologue thereof, or wherein if said first DNA sequence comprises an attR.b sequence or a derivative or homologue thereof said second sequence comprises an attR.b sequence or a derivative or homologue thereof, The method of the present invention may be carried out not only with the naturally occurring attB, attP, attL, and/or attR sequences but also with modified e.g. substituted attB, attP, attL, and/or attR sequences. For example an integrative recombination of the bacteriophage lambda and E. coli between attP and attB homologous sequences (mutants of the wild-type sequences) have been observed which have one or more substitutions in attB (Nash, H. (1981) Annu Rev. Genet., 15, pp. 143; Nussinov, R. and Weisberg, R. (1986) J. Biomol. Struct. Dynamics, 3, pp 1134) and/or in attP (Nash, H. (1981) Annu Rev. Genet., 15, pp. 143).

Thus, the present invention relates to a method wherein the used attB, attP, attP.b, attP.a, attL, attL*, attL.a, attR, attR*, attR.a, and/or attR.b sequences have one or more substitutions in comparison to the naturally occurring attB, attP, attL, and/or attR sequences. Preferred is a method wherein the attB, attP, attP.b, attP.a, attL, attL*, attL.a, attR, attR*, attR.a, and/or attR.b sequences have one, two, three, four, five, six, seven, eight, nine, ten or more substitutions. The substitutions may occur both in the overlap region, in the core region, in the IHF, FIS or XIS factor binding site or in the Int arm binding sites. The complete overlap region comprising seven nucleotides may be substituted also. More preferred is a method wherein substitutions are introduced into attB, attP, attP.b, attP.a, attL, attL*, attL.a, attR, attR*, attR.a, and/or attR.b sequences either in the core region or in the overlap region. Preferred is the introduction of a substitution in the overlap region and the simultaneous introduction of one or two substitutions in the core region. The present invention also relates to a method wherein the used attB, attP, attP.b, attP.a, attL, attL*, attL.a, attR, attR*, attR.a, and/or attR.b sequences are derivatives or homologues, including functional fragments thereof, of said recombination sites in comparison to the naturally occurring attB, attP, attL, and/or attR sequences.

A modification in the form of one or more substitution(s) into recombination sequences is to be chosen such that the recombination can be carried out in spite of the modification(s). Examples for such substitutions are listed e.g. in the publications of Nash, H. (1981), supra and Nussinov, R. and Weisberg, R. (1986), supra and are not considered to be limiting.

Further modifications may be easily introduced e.g. by mutagenesis methods and may be tested for their use by test recombinations.

Furthermore, the present invention relates to a method wherein the used attB, attP, attL, and/or attR sequences or their derivatives or homologues comprise only of one of the respective core Int binding sites, however, more than two core Int binding sites are also preferred. In a preferred embodiment, the present invention relates to a method wherein the used attB, attP, attL, and/or attR sequences or their derivative or homologue s consist only of one of the respective core Int binding sites. In a further embodiment the used attB, attP, attL, and/or attR sequences or their derivative or homologue s consist of two or more core Int binding sites.

The present invention relates further to a method wherein the used attB, attP, attP.b, attP.a, attL, attL*, attL.a, attR, attR*, attR.a, and/or attR.b sequences or their derivatives or homologue s comprise in addition to the core Int binding site one or more, preferably two, three, four, five or more than five, copies of the arm-binding site for Int. Said binding site comprises a consensus motive having the sequence 5'-C/AAGTCACTAT-3' (embodiments disclosed as SEQ ID NOS 5 and 9) or a modified sequence thereof having nucleotide substitutions and being functional with regard to the Int binding. The arm-binding site(s) for Int may be positioned at various distances upstream and/or downstream of the core Int binding site(s).

In order to perform the method of the present invention the first recombination sequence may comprise further DNA sequences which allow the integration into a desired target locus, e.g. in the genome of the eukaryotic cell or an artificial-/minichromosome. This recombination occurs e.g. via the homologous recombination which is mediated by internal cellular recombination mechanisms. For said recombination, the further DNA sequences have to be homologous to the DNA of the target locus and located both 3' and 5' of the attB, attL, attP, attR, attP.b, attP.a, attL*, attL.a, attR*, attR.a or attR.b or derivative or homologue s thereof, respectively. The person skilled in the art knows how great the degree of the homology and how long the respective 3' and 5' sequences have to be such that the homologous recombination occurs with a sufficient probability; see review of Capecchi, M. (1989) Science, 244, pp. 1288.

However, it is also possible to integrate the first recombination sequence by any other mechanism into the genome of the eukaryotic cell, or any artificial-/minichromosome, e.g. via random integration which is also mediated by internal cellular recombination events. Integration of said first recombination site via sequence-specific recombination using sites different from those being integrated, e.g. by using loxP/FRT sequences, is also conceivable.

The second recombination sequence may also comprise DNA sequences which are necessary for an integration into a desired target locus via homologous recombination. For the method of the present invention both the first and/or the second recombination sequence may comprise the further DNA sequences. Preferred is a method wherein both DNA sequences comprise the further DNA sequences.

Introduction of the first and second recombination sequence with or without further DNA sequences may be performed both consecutively and in a co-transformation wherein the recombination sequences are present on two different DNA molecules. Preferred is a method, wherein the first and second recombination sequence with or without further DNA sequences are present and introduced into the eukaryotic cells on a single DNA molecule. Furthermore, the first recombination sequence may be introduced into a cell and the second recombination sequence may be introduced into another cell wherein the cells are fused subsequently. The term fusion means crossing of organisms as well as cell fusion in the widest sense.

The method of the present invention may be used e.g. to invert a DNA segment lying between the indirectly orientated recombination sequences in an intramolecular recombination. Furthermore, the method of the present invention may be used to delete the DNA segment lying between the directly orientated recombination sequences in an intramolecular recombination. If the recombination sequences are each incorporated in 5'-3' or in 3'-5' orientation they are present in direct orientation. The recombination sequences are in indirect orientation if e.g. the attB sequence is integrated in 5'-3' and the attP sequence is integrated in 3'-5' orientation. If the recombination sequences are each incorporated e.g. via homologous recombination into intron sequences 5' and 3' of an exon and the recombination is performed by an integrase, the exon would be inverted in case of indirectly orientated recombination sequences and deleted in case of directly orientated recombination sequences, respectively. With this procedure the polypeptide encoded by the respective gene may lose its activity or function or the transcription may be stopped by the inversion or deletion such that no (complete) transcript is generated. In this way e.g. the biological function of the encoded polypeptide may be investigated. Moreover, inversion or deletion reactions may be used to activate the expression of a gene encoding a desired polypeptide, e.g. by functional linkage of the open reading frame of the encoded polypeptide with regulatory elements which allow transcription and/or translation of the encoded polypeptide. Those regulatory elements include but are not limited to a promotor and or promotor/enhancer elements, which are well known in the art for various eukaryotic expression systems.

However, the first and/or second recombination sequence may comprise further nucleic acid sequences encoding one or more polypeptides/products of interest. For example a structural protein, an enzymatic or a regulatory protein may be introduced via the recombination sequences into the genome being transiently or stably expressed after intramolecular recombination. The introduced polypeptide/product may be an endogenous or exogenous one. Furthermore, a marker protein or biopharmaceutically relevant therapeutic polypeptides may be introduced. The person skilled in the art knows that this listing of applications of the method according to the present invention is only exemplary and not limiting.

Furthermore, the method of the present invention may be used to delete or invert DNA segments on vectors by an intramolecular recombination on episomal substrates. A deletion reaction may be used e.g. to delete packaging sequences from so-called helper viruses. This method has a broad application in the industrial production of viral vectors for gene therapeutic applications.

The intermolecular recombination leads to the fusion of two DNA molecules each having a copy of attB, attP, attL, attR, attP.b, attP.a, attL*, attL.a, attR*, attR.a or attR.b or various combinations of att sequences or of their derivates or homologues. For example, attB or a derivative or homologue thereof may be introduced first via homologous recombination in a known, well characterized genomic locus of a cell or an artificial-/minchromosome. Subsequently an attB, attP, attL, attR, attP.b, attP.a, attL*, attL.a, attR*, attR.a or attR.b carrying vector or DNA-segment may be integrated into said genomic attB sequence via intermolecular recombination. Preferred in this method is the co-expression of the mutant integrase, e.g. Int-h or Int-h/218 within the eukaryotic cell, wherein the recombination occurs. Most preferred is the co-expression of the mutant integrase Int-h/218. Genes encoding for any of those mutant integrases may be located on a second DNA vector being transfected, preferably co-transfected, or on the vector or DNA-segment carrying the attP, attL, attR, attB, attP.b, attP.a, attL*, attL.a, attR*, attR.a or also an attR.b sequence or an derivative or homologue thereof. Further sequences may be located on the attB, attP, attL, attR, attP.b, attP.a, attL*, attL.a, attR*, attR.a or attR.b carrying vector or DNA-segment, e.g. a gene for a particular marker protein flanked by loxP/FRT sequences. With this approach it may be achieved that, e.g. in comparative expression analyses of different genes in a cell type, said genes are not influenced by positive or negative influences of the respective genomic integration locus. Furthermore, the method of the present invention may be used to fuse DNA segments on vectors by an intermolecular recombination on episomal substrates. A fusion reaction may be used e.g. to express recombinant proteins or relevant domains in order to screen for phenotypes. This method may be used in the high throughput analysis of protein functions in eukaryotic cells and is thus of considerable interest.

As mentioned above, intermolecular recombination may be used to introduce one or more gene(s) of interest encoding one or more desired polypeptide(s)/product(s) into, e.g. episomal substrates, artificial-/minichromosomes, or various host cell genomes containing a first recombination sequence. In this context a second DNA comprises beside at least one recombination sequence, e.g. attP, attB, attL, attR, attP.b, attP.a, attL*, attL.a, attR*, attR.a, attR.b or any derivative or homologue thereof, one or more expression cassette(s) for the expression of one or more desired protein(s)/product(s). That expression cassette may be introduced into a desired target locus via the recombination sequences which allows sequence-specific recombination between the DNA comprising the second recombination sequence and the expression cassette, and the first recombination sequence being introduced before into said episomal substrate, artificial-/minichromosome, or host cell genome. This embodiment may be of high interest for establishing high expression cell lines which are suitable for the production of biopharmaceutical products.

In this context, a first DNA comprising at least one recombination sequence has to be introduced, e.g. by random integration, into the genome of the host cell, an artificial-/minichromosomes or episomal substrates contained within the host cell. Alternatively, host cell may be transformed with an artificial-/minichromosome or episomal substrate comprising a corresponding at least one recombination site(s). Another way to integrate recombination sequence(s) into a desired target locus, recognized by a bacteriophage lambda integrase Int, is to use homologous recombination techniques as mentioned above.

To facilitate selection for stable transfectants which have introduced recombination sequence(s) into a desired target locus, a selection marker gene is co-introduced into the same target locus at the same time. This may be achieved, for example, if the recombination sequence(s) and a selection marker gene are co-located on the same vector or DNA segment, which is introduced into the target locus, e.g. by any method mentioned above (homologous recombination, random integration, etc.). As the expression level of the selection marker gene correlates with the transcription activity at the integration site, cells showing a high expression level at site of integration, cell robustness, and good growth characteristics, e.g. in a bioreactor, can be identified very effectively. The level of expression of the selection marker gene can be determined by methods well known in the art, e.g. on the basis of either the amount of corresponding mRNA that is present in the cell, or the amount of polypeptide encoded by the gene. For example, mRNA transcribed from the introduced gene sequence can be quantified by Northern blot hybridization, ribonuclease RNA protection, in situ hybridization to cellular RNA or by PCR. Proteins encoded by a selected sequence can be quantified by various methods, e.g. by ELISA, by Western blotting, by radioimmunoassays, by immunoprecipitation, by assaying for the biological activity of the protein, by immunostaining of the protein followed by FACS analysis, or by measuring the fluorescence signals of a fluorescent protein. By such a method excellent candidates of a production cell line for producing biopharmaceuticals may be obtained.

The integrated recombination sequence(s) (first recombination sequence(s)) allow integration of a further DNA molecule, e.g. a vector or DNA segment carrying at least one further recombination sequence (second recombination sequence) via sequence-specific recombination by a bacteriophage lambda integrase Int into a transcriptional active locus. Preferably, that further DNA molecule comprising at least one second recombination sequence further comprises an expression cassette for the expression of at least one biopharmaceutically relevant gene of interest. For this, host cells, which comprise the first integrated recombination sequence, preferably integrated into the host cell genome at a transcriptional active locus, are tranfected with a DNA molecule comprising the second recombination sequence for a bacteriophage lambda integrase Int, and are cultivated under conditions that allow sequence-specific recombination between the first and the second recombination sequence, preferably the integration of the DNA molecule comprising the second recombination sequence into the host cell genome comprising the first recombination sequence. First and second recombination sequences can be either attP, attB, attL, attR, attP.b, attP.a, attL*, attL.a, attR*, attR.a, attR.b or any derivative or homologue thereof, which allows sequence-specific recombination by a bacteriophage lambda integrase Int or any functional mutant thereof. For example, if the first recombination sequence comprises attP or a derivative or homologue thereof second may comprises attP, attB, attL, attR, attP.b, attP.a, attL*, attL.a, attR*, attR.a, attR.b or any derivative or homologue thereof.

Preferred is the method wherein the sequence-specific recombination is performed by Int, or by Int and XIS, FIS and/or IHF. Most preferred is the method wherein the sequence-specific recombination is performed by Int or by Int and a XIS factor, or by Int and IHF, or by Int and XIS and IHF. Further preferred is the method wherein the sequence-specific recombination is performed by a modified Int, preferably the Int-h or Int-h/218. In this context, use of a modified Int together with XIS and/or IHF is also within the meaning of the present invention.

By this approach any DNA sequence(s), comprising a second recombination sequence for the bacteriophage lambda integrase Int is/are integrated into a known, well characterized and defined locus of the host cell. To select for cells where a sequence-specific recombination has occurred one can introduce, for example, a non-functional expression cassette comprising the selection marker gene, e.g. without a promoter or promoter/enhancer or only part of the coding region of the gene. Only if sequence-specific recombination has occurred, a complete and functional expression cassette with efficient expression of the selection marker gene will be generated, thus allowing for the selection of cells having integrated the gene of interest via sequence specific integration.

By the method of the present invention production cell lines are obtainable differ from the host cell merely by the identity of DNA sequences integrated at a defined site of integration, e.g. into a genomic locus. Due to less genetic variation between different cell clones a more generic process for the development of production cell lines can be used, thus reducing time and capacity for clone selection and development of an optimized production process. The production cell lines may be used for the manufacturing of the desired polypeptide(s).

A further aspect of the present invention therefore relates to a method of expressing at least one gene of interest encoding one or more desired polypeptide(s)/products(s) in a eukaroytic cell, comprising a) introducing a first DNA comprising an attB, attP, attP.b, attP.a, attL, attL*, attL.a, attR, attR*, attR.a or attR.b sequence or a derivative or homologue thereof into a cell; introducing a second DNA comprising an attP.b, attP.a, attL*, attL.a, attR*, attR.a or attR.b sequence or a derivative or homologue thereof, and at least one gene of interest into a cell, contacting said cell with a bacteriophage lambda integrase Int;

performing the sequence-specific recombination by a bacteriophage lambda integrase Int, wherein the second DNA is integrated into the first DNA; and cultivating said cell under conditions, wherein the gene(s) of interest is/are being expressed.

Preferred is that method, wherein if said first DNA sequence comprises an attP.b sequence or a derivative or homologue thereof said second sequence comprises an attB, attP, attP.b, attP.a, attL, attL*, attL.a, attR, attR*, attR.a or attR.b sequence or a derivative or homologue thereof, or wherein if said first DNA sequence comprises an attP.a sequence or a derivative or homologue thereof said second sequence comprises attB, attP, attP.b, attP.a, attL, attL*, attL.a, attR, attR*, attR.a or attR.b sequence or a derivative or homologue thereof, or wherein if said first DNA sequence comprises an attL* sequence or a derivative or homologue thereof said second sequence comprises an attB, attP, attP.b, attP.a, attL, attL*, attL.a, attR, attR*, attR.a or attR.b sequence or a derivative or homologue thereof, or wherein if said first DNA sequence comprises an attL.a sequence or a derivative or homologue thereof said second sequence comprises an attB, attP, attP.b, attP.a, attL, attL*, attL.a, attR, attR*, attR.a or attR.b sequence or a derivative or homologue thereof, or wherein if said first DNA sequence comprises an attR* sequence or a derivative or homologue thereof said second sequence comprises an attB, attP, attP.b, attP.a, attL, attL*, attL.a, attR, attR*, attR.a or attR.b sequence or a derivative or homologue thereof, or wherein if said first DNA sequence comprises an attR.a sequence or a derivative or homologue thereof said second sequence comprises an attB, attP, attP.b, attP.a, attL, attL*, attL.a, attR, attR*, attR.a or attR.b sequence or a derivative or homologue thereof, or wherein if said first DNA sequence comprises an attR.b sequence or a derivative or homologue thereof said second sequence comprises an attB, attP, attP.b, attP.a, attL, attL*, attL.a, attR, attR*, attR.a or attR.b sequence or a derivative or homologue thereof.

In a more preferred embodiment of that method, the first DNA has been integrated into the genome, an artificial-/ minichromosome or an episomal element of a host cell, preferably at sites showing high transcription activity, before said second DNA is introduced into said cell.

The present invention also relates to a method of expressing at least one or more genes of interest in a host cell, wherein said host cell comprises one an attP.b, attP.a, attL*, attL.a, attR*, attR.a or attR.b sequence or a derivative or homologue thereof integrated into the genome of said host cell, comprising
introducing a DNA comprising an attP.b, attP.a, attL*, attL.a, attR*, attR.a or attR.b sequence or a derivative or homologue thereof, and at least one gene of interest into said cell, contacting said cell with a bacteriophage lambda integrase Int;
performing the sequence-specific recombination by a bacteriophage lambda integrase Int, wherein the second DNA is integrated into the first DNA;
cultivating said cell under conditions, wherein the gene(s) of interest is/are being expressed.

The method may be carried out not only with an attB, attP, attL, attR, attP.b, attP.a, attL*, attL.a, attR*, attR.a or attR.b sequence or a derivative or homologue thereof being integrated into a host cell genome by genetic engineering of said cell, but also with naturally occurring recombination sequence of the genome, e.g. the attH-site described in WO01/16345 (5'-GAAATTCTTTTTGATACTAACTTGTGT-3'; SEQ ID NO:14) or any other recombination sequence, which allows sequence-specific recombination mediated by an Int or any functional mutant thereof.

Those methods are preferred, wherein said sequence-specific recombination is performed by Int or by Int and a XIS factor, or by Int and IHF, or by Int and XIS and IHF. Further preferred is the method wherein the sequence-specific recombination is performed by a modified Int, preferably the Int-h or Int-h/218. In this context, use of a modified Int together with XIS and/or IHF is also within the meaning of the present invention. Int, Int-h or Int-h/218, XIS, and/or IHF may be added to the cell in purified form or being co-expressed by said host cell, wherein the sequence-specific recombination is being performed.

A further embodiment of the above mentioned methods relates to a method, wherein the polypeptide(s)/product(s) which is/are encoded by the gene(s) of interest and being expressed in said host cell, is/are isolated from the cells or the cell culture supernatant, if secreted into the culture medium.

Said production cells are cultivated preferentially in serum-free medium and in suspension culture under conditions which are favorable for the expression of the desired gene(s) and isolating the protein of interest from the cells and/or the cell culture supernatant. Preferably the protein of interest is recovered from the culture medium as a secreted polypeptide, or it can be recovered from host cell lysates if expressed without a secretory signal. It is necessary to purifiy the protein of interest from other recombinant proteins, host cell proteins and contaminants in a way that substantially homogenous preparations of the protein of interest are obtained. As a first step often cells and/or particulate cell debris are removed from the culture medium or lysate. The product of interest thereafter is purified from contaminant soluble proteins, polypeptides and nucleic acids, for example, by fractionation on immunoaffinity or ion-exchange columns, ethanol precipitation, reverse phase HPLC, Sephadex chromatography on silica or on a cation exchange resin such as DEAE. In general, methods teaching a skilled person how to purify a heterologous protein expressed by host cells, are well known in the art. Therefore, the aforementioned method of expressing at least one gene of interest may be added by an additional purification step, wherein the desired polypeptide is purified from the host cells or from cell culture if secreted into the culture medium.

The method of the present invention may be performed in all eukaryotic cells. Cells and cell lines may be present e.g. in a cell culture and include but are not limited to eukaryotic cells, such as yeast, plant, insect or mammalian cells. For example, the cells may be oocytes, embryonic stem cells, hematopoietic stem cells or any type of differentiated cells. A method is preferred wherein the eukaryotic cell is a mammalian cell. More preferred is a method wherein the mammalian cell is a human, simian, murine, rat, rabbit, hamster, goat, bovine, sheep or pig cell. Preferred cell lines or "host cells" for the production of biopharmaceuticals are human, mice, rat, monkey, or rodent cell lines. More preferred are hamster cells, preferably BHK21, BHK TK⁻, CHO, CHO-K1, CHO-DUKX, CHO-DUKX B1, and CHO-DG44 cells or the derivatives/progenies of any of such cell lines. Particularly preferred are CHO-DG44, CHO-DUKX, CHO-K1 and BHK21, and even more preferred CHO-DG44 and CHO-DUKX cells. Furthermore, murine myeloma cells, preferably NS0 and Sp2/0 cells or the derivatives/progenies of any of such cell lines are also known as production cell lines.

Host cells are most preferred, when being established, adapted, and completely cultivated under serum free conditions, and optionally in media which are free of any protein/peptide of animal origin. Commercially available media such as Ham's F12 (Sigma, Deisenhofen, Germany), RPMI-1640 (Sigma), Dulbecco's Modified Eagle's Medium (DMEM; Sigma), Minimal Essential Medium (MEM; Sigma), Iscove's Modified Dulbecco's Medium (IMDM; Sigma), CD-CHO (Invitrogen, Carlsbad, Calif.), CHO-S-SFMII (Invtirogen), serum-free CHO Medium (Sigma), and protein-free CHO Medium (Sigma) are exemplary appropriate nutrient solutions. Any of the media may be supplemented as necessary with a variety of compounds examples of which are hormones and/or other growth factors (such as insulin, transferrin, epidermal growth factor, insulin like growth factor), salts (such as sodium chloride, calcium, magnesium, phosphate), buffers (such as HEPES), nucleosides (such as adenosine, thymidine), glutamine, glucose or other equivalent energy sources, antibiotics, trace elements. Any other necessary supplements may also be included at appropriate concentrations that would be known to those skilled in the art. In the present invention the use of serum-free medium is preferred, but media supplemented with a suitable amount of serum can also be used for the cultivation of host cells. For the growth and selection of genetically modified cells expressing a selectable gene a suitable selection agent is added to the culture medium.

"Desired proteins/polypeptides" or "proteins/polypeptides of interest" of the invention are for example, but not limited to insulin, insulin-like growth factor, hGH, tPA, cytokines, such as interleukines (IL), e.g. IL-1, IL-2, IL-3, IL-4, IL-5, IL-6, IL-7, IL-8, IL-9, IL-10, IL-11, IL-12, IL-13, IL-14, IL-15, IL-16, IL-17, IL-18, interferon (IFN) alpha, IFN beta, IFN gamma, IFN omega or IFN tau, tumor necrosisfactor (TNF), such as TNF alpha and TNF beta, TNF gamma, TRAIL; G-CSF, GM-CSF, M-CSF, MCP-1 and VEGF. Also included is the production of erythropoietin or any other hormone growth factors and any other polypeptides that can serve as agonists or antagonists and/or have therapeutic or diagnostic use. The method according to the invention can also be advantageously used for production of antibodies, such as monoclonal, polyclonal, multispecific and single chain antibodies, or fragments thereof, e.g. Fab, Fab', F(ab)₂, Fc and Fc'-fragments, heavy and light immunoglobulin chains and their constant, variable or hypervariable region as well as Fv- and Fd-fragments Fab fragments (Fragment antigen-binding=Fab) consist of the variable regions of both chains which are held together by the adjacent constant region. These may be formed by protease digestion, e.g. with papain, from conventional antibodies, but similar Fab fragments may also be produced in the mean time by genetic engineering. Further antibody fragments include F(ab')2 fragments, which may be prepared by proteolytic cleaving with pepsin.

Using genetic engineering methods it is possible to produce shortened antibody fragments which consist only of the variable regions of the heavy (VH) and of the light chain (VL). These are referred to as Fv fragments (Fragment variable=fragment of the variable part). Since these Fv-fragments lack the covalent bonding of the two chains by the cysteines of the constant chains, the Fv fragments are often stabilised. It is advantageous to link the variable regions of the heavy and of the light chain by a short peptide fragment, e.g. of 10 to 30 amino acids, preferably 15 amino acids. In this way a single peptide strand is obtained consisting of VH and VL, linked by a peptide linker. An antibody protein of this kind is known as a single-chain-Fv (scFv). Examples of scFv-antibody proteins of this kind are known from the prior art.

In recent years, various strategies have been developed for preparing scFv as a multimeric derivative. This is intended to lead, in particular, to recombinant antibodies with improved pharmacokinetic and biodistribution properties as well as with increased binding avidity. In order to achieve multimerisation of the scFv, scFv were prepared as fusion proteins with multimerisation domains. The multimerisation domains may be, e.g. the CH3 region of an IgG or coiled coil structure (helix structures) such as Leucin-zipper domains. However, there are also strategies in which the interaction between the VH/VL regions of the scFv are used for the multimerisation (e.g. dia-, tri- and pentabodies). By diabody the skilled person means a bivalent homodimeric scFv derivative. The shortening of the Linker in an scFv molecule to 5-10 amino acids leads to the formation of homodimers in which an inter-chain VH/VL-superimposition takes place. Diabodies may additionally be stabilised by the incorporation of disulphide bridges. Examples of diabody-antibody proteins are known from the prior art.

By minibody the skilled person means a bivalent, homodimeric scFv derivative. It consists of a fusion protein which contains the CH3 region of an immunoglobulin, preferably IgG, most preferably IgG1 as the dimerisation region which is connected to the scFv via a Hinge region (e.g. also from IgG1) and a Linker region. Examples of minibody-antibody proteins are known from the prior art.

By triabody the skilled person means a: trivalent homotrimeric scFv derivative. ScFv derivatives wherein VH-VL are fused directly without a linker sequence lead to the formation of trimers.

The skilled person will also be familiar with so-called miniantibodies which have a bi-, tri- or tetravalent structure and are derived from scFv. The multimerisation is carried out by di-, tri- or tetrameric coiled coil structures. In a preferred embodiment of the present invention, the gene of interest is encoded for any of those desired polypeptides mentioned above, preferably for a monoclonal antibody, a derivative or fragment thereof.

In order to perform any embodiment of the present invention, an integrase has to act on the recombination sequences. The integrase or the integrase gene and/or a co-factor or a co-factor gene, e.g. the XIS factor or the XIS factor gene and/or IHF or the IHF gene may be present in the eukaryotic cell already before introducing the first and second recombination sequence. They may also be introduced between the introduction of the first and second recombination sequence or after the introduction of the first and second recombination sequence. Purification of recombinase and host factor proteins has been described in the art (Nash, H.A. (1983) Methods of Enzymology, 100, pp. 210; Filutowicz, M. et al. (1994) Gene, 147, pp. 149). In cases when they are not known, cell extracts can be used or the enzymes can be partially purified using procedures described for example for Int or Cre recombinase. The purified proteins can be introduced into a cell by standard techniques, for example by means of injection or microinjection or by means of a lipofection as described in example 3 of WO2004/048584 for IHF. Alternatively the mRNA encoding for the integrase or the host factors can be introduced into the cell. The integrase used for the sequence-specific recombination is preferably expressed in the cell in which the reaction is carried out. For that purpose a third DNA sequence comprising an integrase gene is introduced into the cells. If the sequence specific recombination is carried out e.g. with attL/attR a XIS factor gene (fourth DNA sequence) may be introduced into the cells in addition. Most preferred is a method wherein the third and/or fourth DNA sequence is integrated into the eukaryotic genome of the cell or an artificial-/minichromosome via homologous recombination or randomly. Further preferred is a method wherein the third and/or fourth DNA sequence comprises regulatory sequences resulting in a spatial and/or temporal expression of the integrase gene and/or XIS factor gene.

In this case a spatial expression means that the Int recombinase, the XIS factor, and/or the IHF factor, respectively, is expressed only in a particular cell type by use of cell type specific promotors and catalyzes the recombination only in these cells, e.g. in liver cells, kidney cells, nerve cells or cells of the immune system. In the regulation of the integrase/XIS factor/IHF expression a temporal expression may be achieved by means of promotors being active from or in a particular developmental stage or at a particular point of time in an adult organism. Furthermore, the temporal expression may be achieved by use of inducible promotors, e.g. by interferon or tetracycline depended promotors.

The integrase used in the method of the present invention may be both the wild-type and the modified (mutated) integrase of the bacteriophage lambda. As the wild-type integrase is only able to perform the recombination reaction at a high efficiency with a co-factor, namely IHF, it is preferred to use a modified integrase in the method of the present invention. If the wild-type integrase is used in the method of the present invention, IHF may be needed in addition to achieve a stimulation of the recombination reaction. The modified integrase is modified such that said integrase may carry out the recombination reaction without IHF or other host factors such as XIS and FIS. For example, a recombination reaction between attL and attR sequences may be preformed by a modified Int without the addition of a host factor (see WO2004/048584).

The generation of modified polypeptides and screening for the desired activity is state of the art and may be performed easily. For example, a nucleic acid sequence encoding for a modified integrase is intended to include any nucleic acid sequence that will be transcribed and translated into an integrase either in vitro or upon introduction of the encoding sequence into bacteria or eukaryotic cells. The modified integrase protein encoding sequences can be naturally occurring (by spontaneous mutation) or recombinantly engineered mutants and variants, truncated versions and fragments, functional equivalents, derivatives, homologs and fusions of the naturally occurring or wild-type proteins as long as the biological functional activity, meaning the recombinase activity, of the encoded polypeptide is maintained. Recombinase activity is maintained, when the modified recombinase has at least 50%, preferably at least 70%, more preferred at least 90%, most preferred at least 100% of the activity of the wild-type integrase Int, measured in a co-transfection assay with substrate vectors and expression vectors as described in the examples of the present invention or in Example 3 of WO 01/16345 and/or Results 5.2. Certain amino acid sequence substitutions can be made in an integrase or its underlying nucleic acid coding sequence and a protein can be obtained with like properties. Amino acid substitutions that provide functionally equivalent integrase polypeptides by use of the hydropathic index of amino acids (Kyte, J. et al. (1982) J. Mol. Biol., 157, pp. 105) can be prepared by performing site-specific mutagenesis or polymerase chain reaction mediated mutagenesis on its underlying nucleic acid sequence. In the present invention mutants or modified integrases are preferred, which show in comparison to a wild-type protein improved recombinase activity/recombination efficiency or an recombination activity independent of one or more host factors. "Wild-type protein" means a complete, non truncated, non modified, naturally occurring gene of the encoding polypeptide. Two Int mutants preferred are bacteriophage lambda integrases designated as Int-h and Int-h/218; Miller et al. (1980) Cell, 20, pp. 721; Christ, N. and Droge, P. (1999) J. Mol. Biol., 288, pp. 825. Int-h includes a lysine residue instead of a glutamate residue at position 174 in comparison to wild-type Int. Int-h/218 includes a further lysine residue instead of a glutamate residue at position 218 and was generated by PCR mutagenesis of the Int-h gene. Said mutants may catalyze the recombination between attB/attB, attP/attP, attL/attL or attR/attR and all other possible combinations, e.g. attP/attR, attL/attP, attL/attB, or attR/attB or the derivative or homologue s thereof without the co-factors IHF, XIS, and/or FIS and negative supercoiling in *E. coli*, in eukaryotic cells, and in vitro, i.e. with purified substrates in a reaction tube. An improvement of the efficiency of the recombination may be achieved with a co-factor, e.g. FIS. The mutant Int-h/218 is preferred, because this mutant catalyze the recombination reaction with increased efficiency.

If the first reaction leads to an excision and the used two recombination sequences are identical, e.g. attP.b/attP.b, the resulting recombination sequences after the recombination will be identical to those on the substrate, e.g. here two attP.b sequences. If however, the two partner sequences are different, e.g. attP.b/R, the recombination reaction will generate hybrid recombination sequences which comprise one functional half from one sequence (e.g. attP.b) and one half from the other (attR). A functional half recombination site can be defined as the sequence either 5' or 3' form the overlap, whereby the overlap is considered, in each case, as a part of a functional half-site. If the respective overlap region of the used recombination sequences is identical the excision reaction may be performed with any recombination sequence according to the invention. Additionally, the overlap region designates the orientation of the recombination sequences to each other also, i.e. inverted or direct. The reaction may be performed with wilt-type Int with low efficiency only, however, the addition of IHF or in the absence of IHF the presence of arm binding site(s) in addition to the core binding site stimulates and increases the efficiency. The reaction may be performed without any cofactor by a modified Int.

Furthermore, a method is preferred wherein a further DNA sequence comprising a X is factor gene is introduced into the cells. Most preferred is a method wherein the further DNA sequence further comprises a regulatory DNA sequence giving rise to a spatial and/or temporal expression of the X is factor gene.

For example, after successful integrative intramolecular recombination (inversion) by means of Int leading to the activation/inactivation of a gene in a particular cell type said gene may be inactivated or activated at a later point of time again by means of the induced spatial and/or temporal expression of XIS with the simultaneously expression of Int.

Furthermore, the invention relates to the use of any recombination sequences or the derivative or homologue thereof, e.g. to the derivative or homologue of attP.b as specified in SEQ ID NO: 3 in a sequence specific recombination of DNA in eukaryotic cells. The eukaryotic cell may be present in a cell aggregate of an organism, e.g. a mammal or plants, having no integrase or X is factor in its cells. Said organism may be used for breeding with other organisms having in their cells the integrase or the X is factor so that off-springs are generated wherein the sequence specific recombination is performed in cells of said off-springs. Thus, the invention relates also to the use of an integrase or an integrase gene and a X is factor or a X is factor gene and an IHF factor or an IHF factor gene in a sequence specific recombination in eukaryotic cells. Furthermore, the present invention relates to eukaryotic cells and cell lines in which the method of the present invention was performed, wherein said cells or cell lines are obtained after performing the method of the present invention.

The practice of the present invention will employ, unless otherwise indicated, conventional techniques of cell biology, molecular biology, cell culture, immunology and the like which are in the skill of one in the art. These techniques are fully disclosed in the current literature. All publications and patent applications mentioned in this specification are indicative of the level of skill of those skilled in the art to which this invention pertains. All publications and patent applications cited herein are hereby incorporated by reference in their entirety in order to more fully describe the state of the art to which this invention pertains. The invention generally described above will be more readily understood by reference to the following example, which is hereby included merely for the purpose of illustration of certain embodiments of the present invention and is not intended to limit the invention in any way.

EXAMPLES

Methods

Cell Culture and Transfection

CHO-DG44/dhfr$^{-/-}$ cells (Urlaub, G. et al., (1983), Cell, 33, pp. 405), are grown permanently in suspension in the serum-free medium CHO-S-SFMII (Invitrogen GmbH, Karlsruhe, Del.) supplemented with hypoxanthine and thymidine (HT), are incubated in cell culture flasks at 37° C. in a humidified atmosphere containing 5% $CO_2$. The cell number as well as the cell viability are determined via Cedex (Innovatis). Cells are seeded at a concentration of $1-3\times10^5$ cells/mL in fresh medium every two to three days.

Transient transfections of CHO-DG44 cells are conducted using Lipofectamine Plus reagent (Invitrogen). Per transfection $6\times10^5$ exponentially growing cells in 0.8 mL hypoxanthine/thymidine (HT)-supplemented CHO-S-SFMII medium are seeded in a well of a 6-well chamber. A mixture of plasmid DNAs, 4 µL Lipofectamine and 6 µL Plus reagent in a volume of 200 µL is generated for each transfection and added to the cells, following the protocol of the manufacturer. After incubation for 3 hours 2 mL of HT-supplemented CHO-S-SFMII medium is added.

Isolation of Plasmid DNA from Transfected CHO-DG44 Cells

Cells for the isolation of plasmid DNA are harvested 48 h post transfection and cells (1.5 mL cell suspension) are pelleted by centrifugation in a microcentrifuge at 7000 rpm for 1 minute. For cell lysis and extraction of the plasmid DNA the QIAprep Spin Miniprep is used according to the protocol of the manufacturer (Qiagen). The plasmid DNA is eluted in 100 µL EB buffer.

PCR

Isolated plasmid DNA extracted from transfected cell pools serves as template in a PCR to detect intermolecular recombination. The reaction set-up is as follows:
- 1.0 µL plasmid DNA
- 0.5 µL primer CENfor2 (10 µM; SEQ NO: 15)
- 0.5 µL primer ZsGrev1 (10 µM; SEQ NO: 16)
- 10.5 µL dH₂0
- 12.5 µL 2× GoTaq Green Mastermix (Promega)

Initial denaturation at 94° C., 30 sec followed by 30 cycles of denaturation (94° C., 10 sec), annealing (60° C., 10 sec) and extension (72° C., 30 sec) and a final extension step at 72° C. for 5 min. 5 µL of each PCR sample is loaded on a 2% agarose gel and separated by electrophoresis.

Vector Systems pBI-26/attP: contains CMV promoter and consecutively an attP sequence (SEQ ID No: 2)
pBI-26/attP.b: contains CMV promoter and consecutively the attP variant attP.b (SEQ ID No: 3)
pBI-26/attP.a: contains CMV promoter and consecutively the attP variant attP.a (SEQ ID No: 4)
pBI-26/attL: contains CMV promoter and consecutively the attL sequence (SEQ ID No: 12)
pBI-26/attL.a: contains CMV promoter and consecutively the attL variant attL.a (SEQ ID No: 7)
pZsGreen/attB: contains promoter-less fluorescent green protein with an attB-sequence (SEQ ID NO: 1) upstream of the start codon
pZsGreen/attP.b: contains promoter-less fluorescent green protein with the attP variant attP.b (SEQ ID NO: 3) upstream of the start codon
pZsGreen/attP.a: contains promoter-less fluorescent green protein with the attP variant attP.a (SEQ ID NO:4) upstream of the start codon
pZsGreen/attR: contains promoter-less fluorescent green protein with an attR-sequence (SEQ ID NO: 13) upstream of the start codon
pZsGreen/attR.a: contains promoter-less fluorescent green protein with the attR variant attR.a (SEQ ID NO: 10) upstream of the start codon
pZsGreen/attR.b: contains promoter-less fluorescent green protein with the attR variant attR.b (SEQ ID NO: 11) upstream of the start codon
pBI-26/ZsGreen: positive control and for determination of transfection efficiency; expresses fluorescent green protein under the control of a CMV promoter
pCMV SS Inth218: expresses lambda Integrase Int-h/218 under the control of a CVM promoter
pIHF: expresses IHF with C-terminal His-Tag under the control of a CMV enhancer/beta-actin promoter (chicken)
pBI/TI-X: expresses XIS (excision factor) under the control of a CMV enhancer/UbS27a promoter (hamster)

Example 1

Intermolecular Recombination Using the attP-Variant attP.b in CHO-DG44 Cells

The attP variant attP.b (SEQ ID NO: 3) contains 9 substitutions in comparison to the attP wildtype sequence (SEQ ID NO: 2). This is equivalent to a sequence homology of 96.3% (FIG. 1):

gctgttacaggtcactaataccatctacgtagttgattcatattgtct gcatatcttgtgttttacagtattatctagtctgtttttatccaaaa tctaatttattatattgatatttatatcattttacgtttctcgttcag cttttttatactaagttggcattataaaaaagcattgcttatcaattt gttgcaacgaacaggtcactatcagtcaaaatataatcattatttgat ttc It is being tested whether the attP variant attP.b can still recombine with another recombination site in suspension adapted CHO-DG44 cells under serum free culture conditions because the 9 substitutions are located in the binding sites for IHF, XIS, FIS and Int. For catalysis of the recombination reaction lambda integrase, specifically Int-h/218 integrase, is used.

First, the CHO-DG44 cells are transfected with lambda integrase Int-h/218 and IHF encoding plasmids. Three different types of transfected cell pools are generated:
- transfection using 1 µg pCMV SS Inth218 each per cell pool
- transfection using 450 ng pCMV SS Inth218 and 600 ng pIHF each per cell pool
- mock-transfected cell pools without adding any plasmid (serve as control for background fluorescence)

After 24 hours post first transfection, those cell pools are transfected again using the following combinations of substrate vectors, which contain recombination sequences:
a) pBI26/ZsGreen (=serves as positive control) (500 ng)
b) pBI-26/attP (500 ng)+pZsGreen/attB (500 ng)
c) pBI-26/attP.b (500 ng)+pZsGreen/attB (500 ng)
d) pBI-26/attP.b (500 ng)+pZsGreen/attP.b (500 ng)

Every plasmid combination is inserted in each of the above listed combinations of transfected cell pools, whereby 6 pools each are transfected per combination. Solely for the mock-transfected cells serving as negative control to measure background fluorescence only 2 pools per substrate vector combination are transfected.

After 48 hours post second transfection, the cells are analysed using a FACScalibur (Becton Dickinson). The analysis of the data is performed using CellQuest-Software (Becton Dickinson).

The transfection efficiency, determined by measuring the fraction of fluorescent cells in cell pools transfected with the positive control vector pBI-26/ZsGreen, is between 20% and 25% in suspension adapted CHO-DG44 cells in serum-free medium As a result of a successful intermolecular integrative recombination between attP and attB, attP.b and attB or attP.b and attP.b recombination sequences, respectively, the fluorescent protein should be placed under the control of the CMV promoter. The resulting expression of the fluorescent protein serves as reporter for a recombination event.

The FACS analysis of the substrate vector transfected cells shows that there are successful intermolecular recombination events between attP and attB, attP.b and attB but also between a pair of attP.b (see FIG. 2).

The fraction of fluorescent cells in those experimental set ups, where the cells were first transfected using a combination of integrase and IHF expression vectors, is on average 1.2% for intermolecular recombinations between attP.b and attB substrate vectors, 1.5% for recombinations between attP.b and attP.b substrate vectors and 1.7% for intermolecular recombinations between attP and attB substrate vectors. For those experimental set ups, where the cells were merely pre-transfected with the integrase expression vector, the portion of fluorescent cells was lower. It was on average 0.3% of the cells for intermolecular recombinations between attP.b and attB substrate vectors, 0.4% for recombinations between attP.b and attP.b substrate vectors and 1.1% for intermolecular recombinations between attP and attB substrate vectors. In all cases described above the background fluorescence was subtracted first based on the FACS analysis of cells, which were transfected using the corresponding plasmids, but without adding the plasmids encoding lambda-integrase and IHF. Surprisingly the attP.b variant was still able to mediate site-specific recombinations with an attB sequence and also with another attP.b sequence even though the substitutions are located in the binding sites for IHF, XIS, FIS and Int.

Example 2

Intermolecular Recombination Using attP Variants attP.a and attP.b and attP Wildtype in CHO-DG44 Cells The attP variant attP.a (SEQ ID NO: 4) contains 9 substitutions in comparison to the attP wildtype sequence (SEQ ID NO: 2). This is equivalent to a sequence homology of 96.3% (FIG. 3):

```
gctgttacaggtcactaataccatctatgtagttgattcatattgtct gcatatcttgtgttttacagtattatctagtctgttttttatccaaaa tctaatttattatattgatatttatatcattttacgtttctcgttcag cttttttatactaagttggcattataaaaaagcattgcttatcaattt gttgcaacgaacaggtcactatcagtcaaaatataatcattatttgat ttc
```

The attP variant attP.b (SEQ ID NO: 3) contains 9 substitutions in comparison to the attP wildtype sequence (SEQ ID NO: 2). This is equivalent to a sequence homology of 96.3% (FIG. 1):

```
gctgttacaggtcactaataccatctacgtagttgattcatattgtct gcatatcttgtgttttacagtattatctagtctgttttttatccaaaa tctaatttattatattgatatttatatcattttacgtttctcgttcag cttttttatactaagttggcattataaaaaagcattgcttatcaattt gttgcaacgaacaggtcactatcagtcaaaatataatcattatttgat ttc
```

It is being tested whether the attP variants can still recombine with an identical second attP variant in suspension adapted CHO-DG44 cells under serum free culture conditions because the substitutions are located in the binding sites for IHF, XIS, FIS and/or Int. For catalysis of the recombination reaction lambda integrase, specifically Int-h/218 integrase, is used.

Suspension adapted CHO-DG44 cells were transfected in serum-free medium with the following combinations of substrate vectors (3 cell pools each), which contain recombination sequences:

a) pBI-26/attP.b (200 ng)+pZsGreen/attP.b (200 ng)

b) pBI-26/attP.a (200 ng)+pZsGreen/attP.a (200 ng)

c) pBI-26/attP (200 ng)+pZsGreen/attP (200 ng)

In all cases cells were co-transfected with the plasmid pCMV SS Inth218 which encodes for the lambda integrase Int-h/218 (300 ng).

72 hours post transfection the cells are analysed using a FACScalibur (Becton Dickinson). The analysis of the data is performed using CellQuest-Software (Becton Dickinson).

As a result of a successful intermolecular integrative recombination between attP.b, attP.a or attP recombination sequence pairs, respectively, the fluorescent protein should be placed under the control of the CMV promoter. The resulting expression of the fluorescent protein serves as reporter for a recombination event.

The FACS analysis of the substrate vector transfected cells shows that there are successful intermolecular recombination events not only between wildtype attP pairs but als between attP.b and attP.a pairs (see FIG. 4).

The fraction of fluorescent cells accounts on average for 2% of the cells for intermolecular recombinations between attP.b substrate vector pairs, for 1.9% of the cells for intermolecular recombinations between attP.a substrate vector pairs and for 1.9% of the cells for intermolecular recombination between attP substrate vector pairs (mean value from 3 transfected cell pools each).

In all cases described above the background fluorescence was subtracted first based on the FACS analysis of cells, which were transfected using the corresponding plasmid combination, but adding an empty vector (300 ng) as a mock plasmid rather than a plasmid expressing the lambda integrase.

Surprisingly all attP variants were still able to mediate site-specific recombinations even though the substitutions are located in the binding sites for IHF, XIS, FIS and/or Int.

Example 3

Intermolecular Recombination Between the attL and attR Variants in CHO-DG44 Cells The attL variant attL.a (SEQ ID NO: 7) shown below contains 1 substitution in comparison to the attL wildtype sequence (SEQ ID NO: 12). This is equivalent to a sequence homology of 99% (FIG. 5):

```
ctgcttttttatactaagttggcattataaaaaagcattgcttatcaa tttgttgcaacgaacaggtcactatcagtcaaaatataatcattattt gatttc
```

The attR variant attR.a (SEQ ID NO: 10) shown below contains 8 substitutions in comparison to the attR wildtype sequence (SEQ ID NO: 13). This is equivalent to a sequence homology of 95.1% (FIG. 6):

```
gctgttacaggtcactaataccatctatgtagttgattcatattgtct gcatatcttgtgttttacagtattatctagtctgtttttatccaaaa tctaatttattatattgatatttatatcattttacgtttctcgttcag cttttttatactaacttg
```

The attR variant attR.b (SEQ ID NO: 11) shown below contains 8 substitutions in comparison to the attR wildtype sequence (SEQ ID NO: 13). This is equivalent to a sequence homology of 95.1% (FIG. 6):

```
gctgttacaggtcactaataccatctacgtagttgattcatattgtct gcatatcttgtgttttacagtattatctagtctgtttttatccaaaa tctaatttattatattgatatttatatcattttacgtttctcgttcag cttttttatactaacttg
```

It is tested if the various attL recombination sites can recombine with the various attR recombination sites in suspension adapted CHO-DG44 cells under serum free culture conditions. For catalysis of the recombination reaction lambda integrase, specifically Int-h/218 integrase, is used.

First, the CHO-DG44 cells are transfected with lambda integrase Int-h/218, IHF encoding and XIS encoding plasmids. Two different types of transfected cell pools are generated:
  a) transfection using 400 ng pCMV SS Inth218, 400 ng pIHF and 400 ng pBI/TI-X each per cell pool
  b) mock-transfected cell pools without adding any plasmid (serve as control for background fluorescence)

After 24 hours post first transfection, those cell pools are transfected again using the following combinations of substrate vectors which contain recombination sequences in equimolar amounts:
a) pBI-26/ZsGreen (=serves as positive control) (650 ng)
b) pBI-26/attL (600 ng)+pZsGreen/attR (350 ng)
c) pBI-26/attL.a (600 ng)+pZsGreen/attR.a (350 ng)
d) pBI-26/attL.a (600 ng)+pZsGreen/attR.b (350 ng)

Every plasmid combination is inserted in each of the above listed combinations of transfected cell pools, whereby 3 pools each are transfected per combination. For the mock-transfected cells serving as negative control to measure background fluorescence only 1 pool per substrate vector combination is transfected.

After 48 hours post second transfection, half of the cells are analysed using a FACScalibur (Becton Dickinson). The analysis of the data is performed using CellQuest-Software (Becton Dickinson).

The transfection efficiency, determined by measuring the fraction of fluorescent cells in cell pools transfected with the positive control vector pBI-26/ZsGreen, is on average 23.8% in suspension adapted CHO-DG44 cells in serum-free medium.

As a result of a successful intermolecular integrative recombination between attL and attR, attL.a and attR.a or attL.a and attR.b recombination sequences, respectively, the fluorescent protein should be placed under the control of the CMV promoter. The resulting expression of the fluorescent protein serves as reporter for a recombination event. The FACS analysis of the substrate vector transfected cells shows that there are successful intermolecular recombination events between all combinations in the test series (FIG. 7).

The fraction of fluorescent cells is on average 3.2% for intermolecular recombinations between attL and attR substrate vectors, 2.3% for intermolecular recombinations between attL.a and attR.a substrate vectors and 1.2% for intermolecular recombinations between attL.a and attR.b substrate vectors. In all cases described above the background fluorescence was subtracted first based on the FACS analysis of cells, which were transfected using the corresponding plasmids, but without adding the plasmids encoding lambda-integrase, IHF and XIS. Based on an average transfection efficiency of 23.8% between 5-13% of the transfected cells show a successful intermolecular recombination not only between wildtype attL and attR substrate vectors but also between substrate vectors containing attL and attR variants. The mean relative ZsGreen fluorescence (X-mean) is considerably increased and ranges between 96 to 216 for cell pools transfected with pairs of substrate vectors (FIG. 7). In comparison, negative controls (mock-transfected cells, no plasmids added) have a mean relative ZsGreen fluorescence of 13 and positive control cells transfected with pBI-26/ZsGreen on average a mean relative ZsGreen fluorescence of 733.

For verification of successful intermolecular recombinations PCR on plasmid DNA isolated from transfected cell pools is performed using the primer combination CENfor2 (SEQ ID NO: 15) and ZsGrev1 (SEQ ID NO: 16). In case of a successful intermolecular recombination between the pair of substrate vectors ZsGreen positioned on the pZsGreen/att-vectors comes under the control of the CMV enhancer/promoter located on the pBI-26/att-vectors with the corresponding attachment site between them. As a consequence, a PCR product with the above mentioned primers should only occur in case of successful recombination events. And indeed, in all cell pools pre-transfected with pCMV SS Inth218, pIHF and pBI/TI-X followed by a second tranfection with pairs of substrate vectors the expected PCR product of 380 bp is detected. No PCR product is obtained in mock pre-transfected cell pools transfected in a second transfection with pairs of substrate vectors.

Example 4

Intermolecular Recombination Between the attL and attB Variants and attP and attR Variants in CHO-DG44 Cells The attL variant attL.a (SEQ ID NO: 7) shown below contains 1 substitution in comparison to the attL wildtype sequence (SEQ ID NO: 12). This is equivalent to a sequence homology of 99% (FIG. 5):

```
ctgcttttttatactaagttggcattataaaaaagcattgcttatcaa tttgttgcaacgaacaggtcactatcagtcaaaatataatcattattt gatttc
```

The attR variant attR.a (SEQ ID NO: 10) shown below contains 8 substitutions in comparison to the attR wildtype sequence (SEQ ID NO: 13). This is equivalent to a sequence homology of 95.1% (FIG. 6):

```
gctgttacaggtcactaataccatctatgtagttgattcatattgtct gcatatcttgtgttttacagtattatctagtctgtttttatccaaaa tctaatttattatattgatatttatatcattttacgtttctcgttcag cttttttatactaacttg
```

The attR variant attR.b (SEQ ID NO: 11) shown below contains 8 substitutions in comparison to the attR wildtype sequence (SEQ ID NO: 13). This is equivalent to a sequence homology of 95.1% (FIG. 6):

```
gctgttacaggtcactaataccatctacgtagttgattcatattgtct gcatatcttgtgttttacagtattatctagtctgtttttatccaaaa tctaatttattatattgatatttatatcattttacgtttctcgttcag cttttttatactaacttg
```

It is tested if in suspension adapted CHO-DG44 cells under serum free culture conditions attP can recombine with attR variants and attB with attL variants. For catalysis of the recombination reaction lambda integrase, specifically Int-h/218 integrase, is used.

First, the CHO-DG44 cells are transfected with lambda integrase Int-h/218, IHF encoding and XIS encoding plasmids. Two different types of transfected cell pools are generated:
  a) transfection using 400 ng pCMV SS Inth218, 400 ng pIHF and 400 ng pBI/TI-X each per cell pool
  b) mock-transfected cell pools without adding any plasmid (serve as control for background fluorescence)

After 24 hours post first transfection, those cell pools are transfected again using the following combinations of substrate vectors which contain recombination sequences in equimolar amounts:
a) pBI-26/ZsGreen (=serves as positive control) (650 ng)
b) pBI-26/attL (600 ng)+pZsGreen/attB (350 ng)
c) pBI-26/attL.a (600 ng)+pZsGreen/attB (350 ng)
d) pBI-26/attP (600 ng)+pZsGreen/attR (350 ng)
e) pBI-26/attP (600 ng)+pZsGreen/attR.a (350 ng)
f) pBI-26/attP (600 ng)+pZsGreen/attR.b (350 ng)

Every plasmid combination is inserted in each of the above listed combinations of transfected cell pools, whereby 3 pools each are transfected per combination. For the mock-transfected cells serving as negative control to measure background fluorescence only 1 pool per substrate vector combination is transfected.

After 48 hours post second transfection cells are analysed using a FACScalibur (Becton Dickinson). The analysis of the data is performed using CellQuest-Software (Becton Dickinson).

The transfection efficiency, determined by measuring the fraction of fluorescent cells in cell pools transfected with the positive control vector pBI-26/ZsGreen, is on average 22% in suspension adapted CHO-DG44 cells in serum-free medium.

As a result of a successful intermolecular integrative recombination between attL and attB, attL.a and attB, attP and attR, attP and attR.a or attP and attR.b recombination sequences, respectively, the fluorescent protein should be placed under the control of the CMV promoter. The resulting expression of the fluorescent protein serves as reporter for a recombination event.

Surprisingly, the FACS analysis of the substrate vector transfected cells shows that there are successful intermolecular recombination events between the non-classical cross-combinations of attL and attB variants and attR and attP variants in the test series (FIG. 8).

The fraction of fluorescent cells is on average 2.3% for intermolecular recombinations between attL and attB substrate vectors, 2% for recombinations between attL.a and attB substrate vectors, 2.3% for recombinations between attP and attR substrate vectors, 1.5% for recombinations between attP and attR.a substrate vectors and 1.1% for recombinations between attP and attR.b substrate vectors. In all cases described above the background fluorescence was subtracted first based on the FACS analysis of cells, which were transfected using the corresponding plasmids, but without adding the plasmids encoding lambda-integrase, IHF and XIS. Based on an average transfection efficiency of 22% between 5-10.5% of the transfected cells show a successful intermolecular recombination not only between variants of attL and attB substrate vectors but also between substrate vectors containing attP and attR variants. The mean relative ZsGreen fluorescence (X-mean) is considerably increased and ranges between 65 to 403 for cell pools transfected with pairs of substrate vectors (FIG. 8). In comparison, negative controls (mock-transfected cells, no plasmids added) have a mean relative ZsGreen fluorescence of 15 and positive control cells transfected with pBI-26/ZsGreen on average a mean relative ZsGreen fluorescence of 640.

Example 5

Verification of Intermolecular Recombination Between attL and attB Variants in CHO-DG44 Cells by PCR Method CHO-DG44 cells are transfected with lambda integrase Int-h/218, IHF encoding and XIS encoding plasmids. Two different types of transfected cell pools are generated:

c) transfection using 400 ng pCMV SS Inth218, 400 ng pIHF and 400 ng pBI/TI-X each per cell pool
  d) mock-transfected cell pools without adding any plasmid (serve as control for background fluorescence)

After 24 hours post first transfection, those cell pools are transfected again using the following combinations of substrate vectors, which contain recombination sequences:
a) pBI-26/attL (600 ng)+pZsGreen/attB (350 ng)
b) pBI-26/attL.a (600 ng)+pZsGreen/attB (350 ng)

Every plasmid combination is inserted in each of the above listed combinations of transfected cell pools, whereby 3 pools each are transfected per combination. Solely for the mock-transfected cells serving as negative control to measure background fluorescence only 1 pool per substrate vector combination is transfected.

After 48 hours post second transfection plasmid DNA is isolated from the transfected cell pools. For verification of successful intermolecular recombination between attL and attB substrate vectors a PCR on the isolated plasmid DNA is performed using the primer combination CENfor2 (SEQ ID NO: 15) and ZsGrev1 (SEQ ID NO: 16). In case of a successful intermolecular recombination between the pair of substrate vectors ZsGreen positioned on the pZsGreen/att-vectors comes under the control of the CMV enhancer/promoter located on the pBI-26/att-vectors with the corresponding attachment site between them. As a consequence, a PCR product with the above mentioned primers should only occur in case of successful recombination events. And indeed, in all cell pools pre-transfected with pCM SS Inth218, pIHF and pBI/TI-X followed by a second tranfection with pairs of substrate vectors the expected PCR product of about 400 bp is detected (FIG. 9). No PCR product is obtained in mock pre-transfected cell pools transfected in a second transfection with pairs of substrate vectors. primer Sequence Table:

| SEQ ID NO: 1 | attB (*E. coli*) |
| SEQ ID NO: 2 | attP (bacterio phage lambda DNA) |
| SEQ ID NO: 3 | attP.b (artificial) |
| SEQ ID NO: 4 | attP.a (artificial) |
| SEQ ID NO: 5 | binding site consensus motive |
| SEQ ID NO: 6 | attL* (artificial) |
| SEQ ID NO: 7 | attL.a (artificial) |
| SEQ ID NO: 8 | attR* (artificial) |
| SEQ ID NO: 9 | binding site consensus motive |
| SEQ ID NO: 10 | attR.a (artificial) |
| SEQ ID NO: 11 | attR.b (artificial) |
| SEQ ID NO: 12 | attL (*E. coli*) |
| SEQ ID NO: 13 | attR (*E. coli*) |
| SEQ ID NO: 14 | att H (homo sapiens DNA) |
| SEQ ID NO: 15 | primer CENfor2 |
| SEQ ID NO: 16 | primer ZsGrev1 |

The invention claimed is:

1. A nucleic acid molecule selected from the group consisting of attP.b (SEQ ID NO:3), attP.a (SEQ ID NO:4), attL.a (SEQ ID NO:7), attR.a (SEQ ID NO:10) and attR.b (SEQ ID NO:11).

2. The nucleic acid molecule according to claim 1, whereby said nucleic acid sequence mediates sequence-specific recombination of DNA in eukaryotic cells and whereby sequence specific recombination is performed by a bacteriophage lambda integrase Int.

3. A vector comprising a nucleic acid molecule according to claim 1.

4. The vector according to claim 3, whereby said vector is a eukaryotic expression vector.

5. The vector according to claim 3, whereby said vector comprises a promoter and/or a heterologous gene of interest and/or a selection marker and/or an enhancer.

6. A cell comprising a nucleic acid molecule according to claim 1 integrated into the genome or in an artificial chromosome or in a minichromosome or in an episomal element or in a vector comprising said nucleic acid molecule.

7. The cell according to claim 6, whereby the cell is a eukaryotic cell.

8. The cell according to claim 7, whereby said eukaryotic cell is a CHO cell selected from CHO wild type, CHO K1, CHO DG44, CHO DUKX-B11 and CHO Pro-5.

9. A method of sequence specific recombination of DNA in a eukaryotic cell, comprising
   a) introducing a DNA comprising a first attB (SEQ ID NO: 1), attP (SEQ ID NO:2), attP.b (SEQ ID NO:3), attP.a (SEQ ID NO:4), attL (SEQ ID NO:12), attL.a (SEQ ID NO:7), attR (SEQ ID NO:13), attR.a (SEQ ID NO:10) or attR.b (SEQ ID NO: 11) sequence into said cell;
   b) introducing a DNA comprising a second attP.b (SEQ ID NO:3), attP.a (SEQ ID NO:4), attL.a (SEQ ID NO:7), attR.a (SEQ ID NO:10) or attR.b (SEQ ID NO:11) sequence into said cell, or vice versa, and
   c) performing the sequence specific recombination by a bacteriophage lambda integrase Int.

10. The method according to claim 9, wherein if said first DNA sequence comprises attB (SEQ ID NO:1) sequence said second sequence comprises attP.b (SEQ ID NO:3), attP.a (SEQ ID NO:4), attL.a (SEQ ID NO:7), attR.a (SEQ ID NO:10) or attR.b (SEQ ID NO:11) or vice versa.

11. The method according to claim 9, wherein if said first DNA sequence comprises an attP.b (SEQ ID NO: 3) sequence said second sequence comprises an attP.b (SEQ ID NO:3), attP.a (SEQ ID NO:4), attL.a (SEQ ID NO:7), attR.a (SEQ ID NO:10) or attR.b (SEQ ID NO:11) or vice versa.

12. The method according to claim 11, wherein if said first DNA sequence comprises an attP.b (SEQ ID NO: 3) sequence said second sequence comprises an attP.b (SEQ ID NO: 3) sequence as well.

13. The method of sequence specific recombination of DNA in a eukaryotic cell having integrated the first att sequence according to claim 9 in an artificial-/minichromosome or the genome of said eukaryotic cell, comprising the steps b) and c) according to claim 9.

14. The method according to claim 9, wherein the first att sequence naturally occurs in the genome of said eukaryotic cell or is introduced previously.

15. The method according to claim 9, wherein said sequence-specific recombination is performed by Int and one or more cofactors selected from XIS, FIS and/or IHF.

16. The method according to claim 9, wherein the sequence-specific recombination is performed by a modified Int.

17. A method of expressing at least one gene of interest encoding one or more desired polypeptide(s)/product(s) in a eukaryotic cell, comprising
   a) introducing a first DNA comprising an attB (SEQ ID NO:1), attP (SEQ ID NO:2), attP.b (SEQ ID NO:3), attP.a (SEQ ID NO:4), attL (SEQ ID NO:12), attL* (SEQ ID NO:6), attL.a (SEQ ID NO:7), attR (SEQ ID NO:13), attR.a (SEQ ID NO:10) or attR.b (SEQ ID NO:11) sequence into said cell;
b) introducing a second DNA comprising an attP.b (SEQ ID NO:3), attP.a (SEQ ID NO:4), attL.a (SEQ ID NO:7), attR.a (SEQ ID NO:10) or attR.b (SEQ ID NO:11) sequence and at least one gene of interest into said cell or vice versa;
c) contacting said cell with a bacteriophage lambda integrase Int;
d) performing the sequence-specific recombination by a bacteriophage lambda integrase Int, wherein the second DNA is integrated into the first DNA; and
e) cultivating said cell under conditions, wherein the gene(s) of interest is/are being expressed.

18. The method according to claim 17, wherein said desired polypeptide(s)/product(s) is/are isolated from the host cell or the cell culture medium.

19. The method according to claim 17, wherein said sequence-specific recombination is performed by Int and one or more cofactors selected from XIS, FIS and/or IHF.

20. The method according to claim 17, wherein the sequence-specific recombination is performed by a modified Int.

21. A method of expressing at least one gene of interest encoding one or more desired polypeptide(s)/product(s) in a eukaryotic cell, having at least one naturally occurring recombination sequence which allows sequence-specific recombination mediated by an bacteriophage lambda Int or any functional mutant thereof, comprising
a) introducing a DNA comprising an attP.b (SEQ ID NO:3), attP.a (SEQ ID NO:4), attL.a (SEQ ID NO:7), attR.a (SEQ ID NO:10) or attR.b (SEQ ID NO:11) sequence and at least one gene of interest into said cell;
b) contacting said cell with a bacteriophage lambda integrase Int;
c) performing the sequence-specific recombination by a bacteriophage lambda integrase Int, between the recombination sequence naturally occurring in said cell and the DNA introduced into said cell; and
d) cultivating said cell under conditions, wherein the gene(s) of interest is/are being expressed.

22. The method of claim 21, wherein the naturally occurring sequence is attH (SEQ ID NO: 14).

23. The method according to claim 21, wherein said sequence-specific recombination is performed by Int and one or more cofactors selected from XIS, FIS and/or IHF.

24. The method according to claim 21, wherein the sequence-specific recombination is performed by a modified Int.

* * * * *

UNITED STATES PATENT AND TRADEMARK OFFICE
CERTIFICATE OF CORRECTION

| | | |
|---|---|---|
| PATENT NO. | : 8,404,486 B2 | Page 1 of 1 |
| APPLICATION NO. | : 12/744754 | |
| DATED | : March 26, 2013 | |
| INVENTOR(S) | : Enenkel | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 285 days.

Signed and Sealed this
Eighth Day of October, 2013

Teresa Stanek Rea
*Deputy Director of the United States Patent and Trademark Office*

SEQUENCE LISTING

```
<160> NUMBER OF SEQ ID NOS: 16

<210> SEQ ID NO 1
<211> LENGTH: 21
<212> TYPE: DNA
<213> ORGANISM: Escherichia coli

<400> SEQUENCE: 1
ctgctttttt atactaactt g                                              21

<210> SEQ ID NO 2
<211> LENGTH: 243
<212> TYPE: DNA
<213> ORGANISM: Bacteriophage lambda

<400> SEQUENCE: 2
tctgttacag gtcactaata ccatctaagt agttgattca tagtgactgc atatgttgtg    60
ttttacagta ttatgtagtc tgttttttat gcaaaatcta atttaatata ttgatattta   120
tatcatttta cgtttctcgt tcagcttttt tatactaagt tggcattata aaaaagcatt   180
gcttatcaat ttgttgcaac gaacaggtca ctatcagtca aaataaaatc attatttgat   240
ttc                                                                  243

<210> SEQ ID NO 3
<211> LENGTH: 243
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: attP.b

<400> SEQUENCE: 3
gctgttacag gtcactaata ccatctacgt agttgattca tattgtctgc atatcttgtg    60
ttttacagta ttatctagtc tgttttttat ccaaaatcta atttattata ttgatattta   120
tatcatttta cgtttctcgt tcagcttttt tatactaagt tggcattata aaaaagcatt   180
gcttatcaat ttgttgcaac gaacaggtca ctatcagtca aaatataatc attatttgat   240
ttc                                                                  243

<210> SEQ ID NO 4
<211> LENGTH: 243
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: attP.a
```

<400> SEQUENCE: 4

```
gctgttacag gtcactaata ccatctatgt agttgattca tattgtctgc atatcttgtg    60
ttttacagta ttatctagtc tgttttttat ccaaaatcta atttattata ttgatattta   120
tatcatttta cgtttctcgt tcagcttttt tatactaagt tggcattata aaaaagcatt   180
gcttatcaat ttgttgcaac gaacaggtca ctatcagtca aaatataatc attatttgat   240
ttc                                                                 243
```

<210> SEQ ID NO 5
<211> LENGTH: 10
<212> TYPE: DNA
<213> ORGANISM: Artificial Sequence
<220> FEATURE:
<223> OTHER INFORMATION: Description of Artificial Sequence: Synthetic
      binding site consensus motif

<400> SEQUENCE: 5

```
cagtcactat                                                           10
```

<210> SEQ ID NO 6
<211> LENGTH: 102
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: att L*

<400> SEQUENCE: 6

```
ctgcttttttg atactaagtt ggcattataa aaaagcattg cttatcaatt tgttgcaacg    60
aacaggtcac tatcagtcaa ataaaatca ttatttgatt tc                       102
```

<210> SEQ ID NO 7
<211> LENGTH: 102
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: attL.a

<400> SEQUENCE: 7

```
ctgcttttttt atactaagtt ggcattataa aaaagcattg cttatcaatt tgttgcaacg    60
aacaggtcac tatcagtcaa aatataatca ttatttgatt tc                      102
```

<210> SEQ ID NO 8
<211> LENGTH: 162
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: attR*

<400> SEQUENCE: 8

```
tctgttacag gtcactaata ccatctaagt agttgattca tagtgactgc atatgttgtg    60
ttttacagta ttatgtagtc tgttttttat gcaaaatcta atttaatata ttgatattta   120
tatcatttta cgtttctcgt tcagcttttt gatactaact tg                      162
```

```
<210> SEQ ID NO 9
<211> LENGTH: 10
<212> TYPE: DNA
<213> ORGANISM: Artificial Sequence
<220> FEATURE:
<223> OTHER INFORMATION: Description of Artificial Sequence: Synthetic
      binding site consensus motif

<400> SEQUENCE: 9
aagtcactat                                                              10

<210> SEQ ID NO 10
<211> LENGTH: 162
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: attR.a

<400> SEQUENCE: 10
gctgttacag gtcactaata ccatctatgt agttgattca tattgtctgc atatcttgtg      60
ttttacagta ttatctagtc tgttttttat ccaaaatcta atttattata ttgatattta     120
tatcatttta cgtttctcgt tcagcttttt tatactaact tg                        162

<210> SEQ ID NO 11
<211> LENGTH: 162
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: attR.b

<400> SEQUENCE: 11
gctgttacag gtcactaata ccatctacgt agttgattca tattgtctgc atatcttgtg      60
ttttacagta ttatctagtc tgttttttat ccaaaatcta atttattata ttgatattta     120
tatcatttta cgtttctcgt tcagcttttt tatactaact tg                        162

<210> SEQ ID NO 12
<211> LENGTH: 102
<212> TYPE: DNA
<213> ORGANISM: Escherichia coli

<400> SEQUENCE: 12 ctgcttttt atactaagtt ggcattataa aaaagcattg cttatcaatt tgttgcaacg      60
aacaggtcac tatcagtcaa aataaaatca ttatttgatt tc                       102

<210> SEQ ID NO 13
<211> LENGTH: 162
<212> TYPE: DNA
<213> ORGANISM: Escherichia coli

<400> SEQUENCE: 13
tctgttacag gtcactaata ccatctaagt agttgattca tagtgactgc atatgttgtg      60
ttttacagta ttatgtagtc tgttttttat gcaaaatcta atttaatata ttgatattta     120
tatcatttta cgtttctcgt tcagcttttt tatactaact tg                        162

<210> SEQ ID NO 14
<211> LENGTH: 27
<212> TYPE: DNA
```

```
<213> ORGANISM: Homo sapiens
<220> FEATURE:
<223> OTHER INFORMATION: att H

<400> SEQUENCE: 14
gaaattcttt ttgatactaa cttgtgt                                          27

<210> SEQ ID NO 15
<211> LENGTH: 23
<212> TYPE: DNA
<213> ORGANISM: Artificial Sequence
<220> FEATURE:
<223> OTHER INFORMATION: Description of Artificial Sequence: Synthetic
      CENfor2 primer

<400> SEQUENCE: 15
gacgtcaatg ggagtttgtt ttg                                              23

<210> SEQ ID NO 16
<211> LENGTH: 20
<212> TYPE: DNA
<213> ORGANISM: Artificial Sequence
<220> FEATURE:
<223> OTHER INFORMATION: Description of Artificial Sequence: Synthetic
      ZsGrev1 primer

<400> SEQUENCE: 16
atccaatgcc ctctcccgtg                                                  20
```